(12) United States Patent
Sugihara et al.

(10) Patent No.: US 9,339,252 B2
(45) Date of Patent: May 17, 2016

(54) X-RAY CT IMAGING DEVICE AND X-RAY CT IMAGING METHOD

(71) Applicant: J. Morita Manufacturing Corporation, Kyoto (JP)

(72) Inventors: Yoshito Sugihara, Kyoto (JP); Hideki Yoshikawa, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 70 days.

(21) Appl. No.: 14/200,989

(22) Filed: Mar. 7, 2014

(65) Prior Publication Data

US 2014/0328446 A1    Nov. 6, 2014

(30) Foreign Application Priority Data

Mar. 8, 2013  (JP) ................. 2013-046862

(51) Int. Cl.
| | |
|---|---|
| *A61B 5/06* | (2006.01) |
| *A61B 5/08* | (2006.01) |
| *G01N 23/04* | (2006.01) |
| *A61B 6/00* | (2006.01) |
| *A61B 6/03* | (2006.01) |
| *A61B 6/14* | (2006.01) |

(52) U.S. Cl.
CPC ................. *A61B 6/542* (2013.01); *A61B 6/032* (2013.01); *A61B 6/14* (2013.01); *A61B 6/501* (2013.01)

(58) Field of Classification Search
CPC ...... A61B 6/032; A61B 6/037; A61B 6/4441; A61B 6/482; A61B 6/027; A61B 6/0414; A61B 6/08; A61B 6/463; A61B 6/5217; A61B 6/5235; A61B 6/5247; A61B 6/541; A61B 6/542; A61B 6/547; A61B 6/03; A61B 6/4035; A61B 5/06; A61B 5/10; A61B 5/1042; A61B 5/1081; A61B 5/01; G01N 23/04; G01N 23/046
USPC ........... 378/4, 62, 108, 151, 5, 901, 147, 150, 378/16; 382/131, 103, 107, 154; 250/336.1, 250/361 R
See application file for complete search history.

(56) References Cited

U.S. PATENT DOCUMENTS

| | | | | |
|---|---|---|---|---|
| 5,317,616 | A * | 5/1994 | Swerdloff | ................ A61B 6/00 378/151 |
| 5,351,280 | A * | 9/1994 | Swerdloff | ............ A61N 5/1042 378/150 |
| 6,507,639 | B1 | 1/2003 | Popescu | |
| 7,545,901 | B2 * | 6/2009 | Mistretta | ............... G06T 11/006 378/4 |
| 7,602,880 | B2 * | 10/2009 | Hirokawa | .............. A61B 6/032 378/108 |

(Continued)

FOREIGN PATENT DOCUMENTS

| | | |
|---|---|---|
| EP | 1393681 A1 | 3/2004 |
| JP | H11-19078 A | 1/1999 |

(Continued)

*Primary Examiner* — David A Vanore
(74) *Attorney, Agent, or Firm* — Osha Liang LLP

(57) ABSTRACT

According to an X-ray imaging device for performing CT imaging, a main body control section controls at least one of an X-ray revolution plane formed by an X-ray cone beam along with the revolution of a revolving arm and a revolution range of the revolving arm in accordance with a CT imaging area accepted by an imaging area setting screen. Such control is performed in order to decrease X-ray radiation to a high sensitivity site in the area that revolves during the CT imaging, the high sensitivity site being positionally set in a biological body as a site that is sensitive to X-rays.

14 Claims, 24 Drawing Sheets

(56) References Cited

U.S. PATENT DOCUMENTS

| | | | | |
|---|---|---|---|---|
| 7,640,607 B2* | 1/2010 | Guertin | A61B 6/032 | 378/209 |
| 8,451,972 B2* | 5/2013 | Dafni | A61B 6/032 | 378/11 |
| 8,503,750 B2 | 8/2013 | Benson | A61B 6/5258 | 378/4 |
| 8,744,039 B2* | 6/2014 | Hirokawa | A61B 6/032 | 378/108 |
| 8,971,601 B2* | 3/2015 | Zaiki | A61B 6/463 | 382/128 |
| 9,025,848 B2* | 5/2015 | Okabe | A61B 6/032 | 378/4 |
| 2003/0198319 A1 | 10/2003 | Toth et al. | | |
| 2005/0117696 A1 | 6/2005 | Suzuki et al. | | |
| 2005/0254621 A1 | 11/2005 | Kalender et al. | | |
| 2008/0267455 A1* | 10/2008 | Grass | A61B 6/032 | 382/107 |
| 2010/0119033 A1* | 5/2010 | Li | A61B 6/06 | 378/5 |
| 2011/0142315 A1* | 6/2011 | Hsieh | A61B 6/032 | 382/131 |
| 2011/0206259 A1* | 8/2011 | Mistretta | A61B 6/032 | 382/131 |
| 2011/0301449 A1* | 12/2011 | Maurer, Jr. | A61B 6/032 | 600/411 |
| 2012/0155605 A1 | 6/2012 | Yazaki | | |
| 2013/0083887 A1* | 4/2013 | Li | A61B 6/032 | 378/19 |
| 2013/0230136 A1* | 9/2013 | Sakaguchi | H04N 13/00 | 378/41 |
| 2013/0266123 A1* | 10/2013 | Yoshida | A61B 6/545 | 378/98.5 |
| 2013/0343622 A1* | 12/2013 | Ruiz | G06T 11/008 | 382/131 |
| 2014/0270365 A1* | 9/2014 | Mostafavi | A61B 6/52 | 382/103 |
| 2014/0328465 A1* | 11/2014 | Herrmann | G01T 1/17 | 378/62 |
| 2014/0362970 A1* | 12/2014 | Launay | A61B 6/5258 | 378/4 |
| 2015/0036786 A1* | 2/2015 | Katcha | A61B 6/56 | 378/4 |

FOREIGN PATENT DOCUMENTS

| | | |
|---|---|---|
| JP | 2003-245277 A | 9/2003 |
| JP | 2006-280478 A | 10/2006 |
| JP | 2007-029168 A | 2/2007 |
| JP | 2010-269048 A | 12/2010 |
| JP | 2011-041598 A | 3/2011 |
| JP | 2012/130542 A | 7/2012 |
| JP | 2012-217572 A | 11/2012 |
| WO | 03/084407 A1 | 10/2003 |
| WO | 2009063974 A1 | 5/2009 |

* cited by examiner

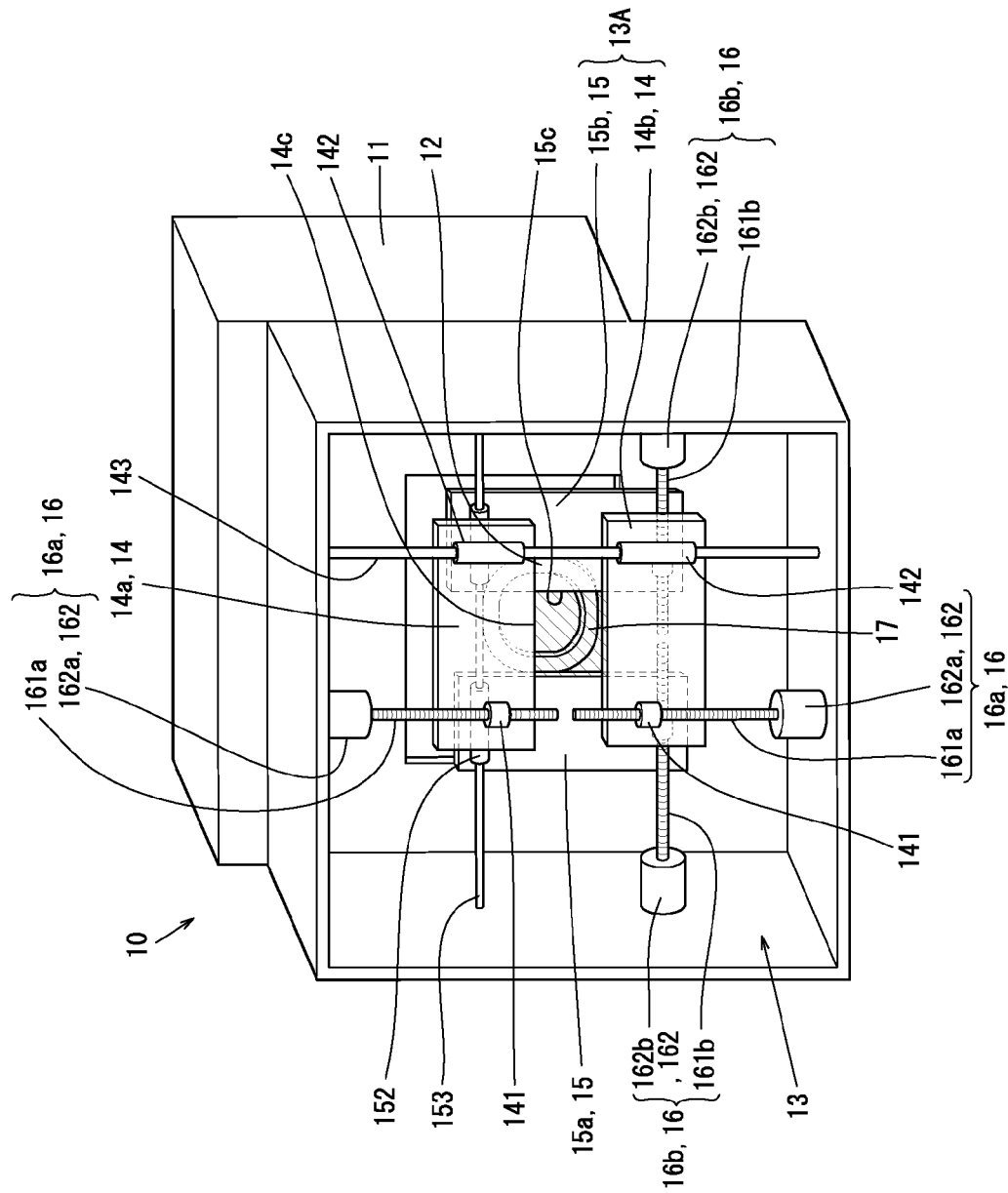

X-RAY CT IMAGING DEVICE AND X-RAY CT IMAGING METHOD

CROSS-REFERENCE TO RELATED APPLICATIONS

The present application claims benefit of priority under 35 U.S.C. §119 to Japanese Patent Application No. 2013-046862 filed on Mar. 8, 2013. The contents of the priority applications are incorporated by reference in their entirety.

BACKGROUND OF THE INVENTION

1. Field of the Invention

The present invention relates to an X-ray CT imaging device and an X-ray imaging method for performing CT imaging by detecting, by an X-ray detector, an X-ray directed from an X-ray generator toward a subject located between the X-ray generator and the X-ray detector.

2. Description of the Prior Art

Conventionally, in the fields of medical care and the like, CT (computerized tomography) imaging is performed. According to the CT imaging, an X-ray beam is directed toward a subject to collect projection data, and the obtained projection data is re-constructed on a computer to generate a CT image (volume rendering image, etc.).

CT imaging is performed as follows. A subject is located between an X-ray generator and an X-ray detector. While the X-ray generator and the X-ray detector are revolved around the subject, a cone-like X-ray beam (X-ray cone beam) is directed toward the subject from the X-ray generator. The results of the X-ray detection (projection data) are collected by the X-ray detector, and three-dimensional data is re-constructed based on the collected X-ray detection results. A device usable for performing such CT imaging is disclosed in, for example, Patent Document 1.

According to Patent Document 1, the CT imaging device described therein operates as follows. During CT imaging, a pair of channel collimators are displaced in front of the X-ray generator such that a CT imaging area (field of view (FOV)), namely, an area irradiated with an X-ray (hereinafter, referred as the "X-ray radiation area"), becomes circular or elliptical. Thus, CT imaging can be performed only on an area of interest of a patient, who is a subject of the CT imaging.

However, there is a case where the area passed by an X-ray cone beam generated by the X-ray detector and revolving, namely, a flux of X-rays revolving during the CT imaging, encompasses a high sensitivity site of a biological body that is sensitive to X-rays such as, for example, submandibular gland, parotid gland, sublingual gland, thyroid gland, or lens of the eyeball. In such a case, especially when the patient has abnormality in such a high sensitivity site, the X-ray flux passing the high sensitivity site exerts a large influence. Therefore, care should be taken when the CT imaging is performed.

PRIOR ART DOCUMENT

Patent Document

Patent Document 1: Japanese Laid-Open Patent Publication No. Hei 11-19078

SUMMARY OF THE INVENTION

One or more embodiments of the present invention provide an X-ray CT imaging device and an X-ray CT imaging method capable of, even when a high sensitivity site is in the vicinity of an X-ray radiation area that is set for an imaging target site, performing CT imaging on the imaging target site while keeping the exposure dose of the high sensitivity site low.

One or more embodiments of the present invention are directed to an X-ray CT imaging device including a revolution section that causes an X-ray generation source and an electric X-ray detector, facing each other while having a subject therebetween, to revolve about a revolution shaft as a center of revolution; a revolution driving section that drives driving the revolution section to revolve with respect to the subject; an X-ray radiation area setting section that accepts a setting of a local area of the subject as an X-ray radiation area; a control section that controls at least the revolution driving section; and a high sensitivity site specification section to specify a high sensitivity site in a biological body that is highly sensitive to an X-ray. The revolution section is revolved with respect to the X-ray radiation area to perform CT imaging. When radiation of an X-ray flux in a revolving movement is performed during the CT imaging in accordance with the X-ray radiation area accepted by the X-ray radiation area setting section, the control section controls at least one of an X-ray revolution plane formed by the X-ray flux along with the revolution of the revolution section, and a revolution range of the revolution section, such that an amount of X-ray radiation toward the high sensitivity site is decreased.

The "X-ray CT imaging device" encompasses an imaging device capable of performing CT imaging with the imaging revolution range of about 180 degrees and about 360 degrees, and an imaging device capable of performing DVT imaging or tomosynthesis imaging with no limitation on the imaging revolution range.

The "revolution driving section that drives the revolution section to revolve with respect to the subject" drives the revolution section to perform horizontal evolution, to perform inclination revolution in which the revolution section is inclined, to move upward and downward and then perform horizontal revolution, and to revolve after the subject is moved upward and downward.

The "high sensitivity site" encompasses a high sensitivity site set at a position by an operation made by an operator and a high sensitivity site selected automatically or semi-automatically from high sensitivity sites at preset positions.

Owing to this, even when a high sensitivity site is in the vicinity of the X-ray radiation area that is set for an imaging target site, CT imaging can be performed on the imaging target site with certainty while keeping the exposure dose of the high sensitivity site low.

This will be described in more detail. The control section controls at least one of the X-ray revolution plane formed by the X-ray flux along with the revolution of the revolution section and the revolution range of the revolution section in order to decrease the X-ray radiation to the high sensitivity site specified by the high sensitivity site specification section when the X-ray radiation is performed toward the X-ray irradiation area accepted by the X-ray radiation area setting section.

In one or more embodiments of the present invention, the high sensitivity site specification section may specify the high sensitivity site in a schematic view of a head of the subject.

The "high sensitivity site specification section to specify the high sensitivity site" encompasses a specification section to specify a high sensitivity site automatically, semi-automatically, by a selection operation made by an operator or by any other operation, from a plurality of registered high sensitivity sites, based on information on the high sensitivity sites such as the position, size, sensitivity or the like, and also encompasses other specification sections to specify information on the high sensitivity sites by various methods.

Owing to this, even when a high sensitivity site is in the vicinity of the X-ray radiation area that is set for an imaging target site, CT imaging can be performed on the imaging target site with certainty while keeping the exposure dose of the high sensitivity site low.

This will be described in more detail. The control section controls at least one of the X-ray revolution plane formed by the X-ray flux along with the revolution of the revolution section and the revolution range of the revolution section in order to decrease the X-ray radiation to the high sensitivity site specified by the high sensitivity site specification section when the X-ray radiation is performed toward the X-ray irradiation area accepted by the X-ray radiation area setting section. Therefore, even when a high sensitivity site specified by the high sensitivity site specification section is in the vicinity of the X-ray radiation area that is set for an imaging target site, CT imaging can be performed on the imaging target site with certainty while keeping the exposure dose of the high sensitivity site low.

In one or more embodiments of the present invention, the control section may perform revolution range control of changing at least one of an X-ray radiation start position and an X-ray radiation end position in the revolution range in accordance with the X-ray radiation area set by the X-ray radiation area setting section and the high sensitivity site.

Owing to this, the revolution range of the revolution section can be adjusted without changing the X-ray revolution plane of the revolution section. Therefore, the exposure dose of the high sensitivity site can be easily decreased.

In one or more embodiments of the present invention, the control section may perform control of changing at least one of an X-ray radiation angle with respect to a predetermined reference plane and a radiation position on the subject to control the x-ray revolution plane in accordance with the X-ray radiation area set by the X-ray radiation area setting section and the high sensitivity site.

The "determined reference plane" is a generally horizontal plane when the subject is standing up or sitting down, and is a generally vertical plane when the subject is lying down.

The "radiation position" on the subject may be a position in a direction intersecting the reference plane on which the revolution section revolves, for example, a position in a height direction when the revolution section revolves in the horizontal direction.

Owing to this, at least one of the X-ray radiation angle with respect to the determined reference plane and the radiation position on the subject is changed, so that the CT imaging can be performed on the imaging target site in the set X-ray radiation area with certainty while the exposure dose of the high sensitivity site in the vicinity of the X-ray radiation area is decreased.

In one or more embodiments of the present invention, the X-ray CT imaging device may further include a support section that supports the revolution section via the revolution shaft; and a support section moving section that moves the support section. The support section moving section may include at least one of a shaft moving mechanism that moves the revolution shaft with respect to the support section and a relative moving mechanism that moves the support section with respect to the subject. The control section may control the movement of the support section moving section thus to control the X-ray revolution plane.

Owing to this, the support section that supports the revolution section via the revolution shaft can be moved by the support section moving section. Therefore, the exposure dose of the high sensitivity site can be easily decreased.

In one or more embodiments of the present invention, the X-ray CT imaging device may further include an X-ray radiation range restriction section that restricts an X-ray radiation range, the X-ray radiation range restriction section being provided forward to the X-ray generation source in an X-ray radiation direction. The control section may control the restriction of the X-ray radiation range restriction section thus to control the X-ray revolution plane.

Owing to this, the X-ray radiation range restricted by the X-ray radiation range restriction section can be changed. Therefore, the exposure dose of the high sensitivity site can be easily decreased.

In one or more embodiments of the present invention, the X-ray CT imaging device may further include a control pattern storage section that stores a control pattern by the control section for each of set areas that are each set as the X-ray radiation area by the X-ray radiation area setting section.

Owing to this, the CT imaging can be performed in such a manner that the exposure dose of the high sensitivity site is decreased by merely setting the X-ray radiation area by use of the X-ray radiation area setting section.

In one or more embodiments of the present invention, the X-ray CT imaging device may further include a high sensitivity site information storage section that stores information on the high sensitivity site.

Owing to this, information on the high sensitivity site such as, for example, the position, size, sensitivity degree, priority level (weighting degree) or the like stored on the high sensitivity site information storage section can be retrieved. Thus, the CT imaging can be performed in such a manner that the exposure dose of the high sensitivity is decreased.

In one or more embodiments of the present invention, the X-ray radiation area setting section may display an image containing the X-ray radiation area and accept a setting that sets the X-ray radiation area with respect to the displayed image, and may also display the high sensitivity site as overlapping the image.

The image may be a scout image, a panorama image, a cephalo image, a schematic illustration or an optically captured photo of the subject, or a combination thereof.

Owing to this, the high sensitivity site displayed as overlapping the image which encompasses the X-ray radiation area can be visually checked. Therefore, the high sensitivity site, the exposure dose of which is to be decreased during the CT imaging, can be specified with more certainty.

In one or more embodiments of the present invention, the X-ray CT imaging device may further include a high sensitivity site replacing section that replaces the high sensitivity site displayed as overlapping the image with another high sensitivity site.

The "high sensitivity site replacing section that replaces the high sensitivity site" may be a replacing section that replaces at least a display or parameter of any of various types of detailed information such as the size, position, sensitivity, priority level (weighting degree) and the like.

Owing to this, the CT imaging can be performed in an appropriate manner in accordance with the situation of the subject. For example, a higher priority level is assigned to a high sensitivity site which is far from the set X-ray radiation area but has abnormality occurring, instead of a high sensitivity site closest to the set X-ray radiation area.

In one or more embodiments of the present invention, the X-ray CT imaging device may further include an X-ray imaging preparation switch that revolves the revolution section to the X-ray radiation start position in the revolution range in accordance with the set area that is set by the X-ray radiation area setting section, the revolution range being different for each of the set areas; and an X-ray radiation switch that directs the X-ray toward the set area while revolving the revolution section to perform imaging.

Owing to this, for example, the revolution section is revolved to the start position of the X-ray radiation range to prepare for imaging, and the revolution section is further revolved by the X-ray radiation switch. Thus, CT imaging can be performed in such a manner that the exposure dose of the high sensitivity site is decreased.

In one or more embodiments of the present invention, the X-ray CT imaging device may further include a movement driving section that moves the revolution section. The control section may perform driving control that moves the revolution section with respect to the movement driving section. In the driving control, controls for both of the revolution of the revolution section and the movement of the revolution section caused by moving the revolution shaft by the movement driving section may be performed concurrently to allow panorama X-ray imaging to be performed.

Owing to this, when a panorama image is needed, panorama X-ray imaging can be performed with no need to prepare another X-ray imaging device.

In one or more embodiments of the present invention, the X-ray CT imaging device may further include a cephalo-imaging head fixation device provided perpendicularly to a direction of the revolution shaft, and thus cephalo-X-ray imaging may be allowed to be performed.

Owing to this, when a cephalogram is needed, cephalo X-ray imaging can be performed with no need to prepare another X-ray imaging device.

One or more embodiments of the present invention are also directed to an X-ray CT imaging method performed by use of an X-ray CT imaging device. The X-ray CT imaging device includes a revolution section that causes an X-ray generation source and an electric X-ray detector, facing each other while having a subject therebetween, to revolve about a revolution shaft as a center of revolution; a revolution driving section that drives the revolution section to revolve with respect to the subject; an X-ray radiation area setting section that accepts a setting of a local area of the subject as an X-ray radiation area; and a control section that controls at least the revolution driving section. The revolution section is revolved with respect to the X-ray radiation area to perform CT imaging. The X-ray CT imaging method includes the step of, when a high sensitivity site of a biological body that is highly sensitive to an X-ray is located in an area where an X-ray flux in a revolving movement passes during the CT imaging in accordance with the X-ray radiation area accepted by the X-ray radiation area setting section, controlling at least one of an X-ray revolution plane formed by the X-ray flux along with the revolution of the revolution section and a revolution range of the revolution section, such that an amount of X-ray radiation toward the high sensitivity site is decreased in accordance with the X-ray radiation area accepted by the X-ray radiation area setting section, the control being performed by the control section.

Owing to this, even when a high sensitivity site is in the vicinity of the X-ray radiation area that is set for an imaging target site, CT imaging can be performed on the imaging target site with certainty while keeping the exposure dose of the high sensitivity site low.

One or more embodiments of the present invention provide an X-ray CT imaging device and an X-ray CT imaging method capable of, even when a high sensitivity site is in the vicinity of an X-ray radiation area that is set for an imaging target site, performing CT imaging on the imaging target site while keeping the exposure dose of the high sensitivity site low.

BRIEF DESCRIPTION OF DRAWINGS

FIG. 4 is a schematic isometric view of a beam formation mechanism.

DESCRIPTION OF THE PREFERRED EMBODIMENTS

Hereinafter, an X-ray CT imaging device and an X-ray CT imaging method according to one or more embodiments of the present invention will be described with reference to FIG. 1 through FIG. 17.

Figure 1:
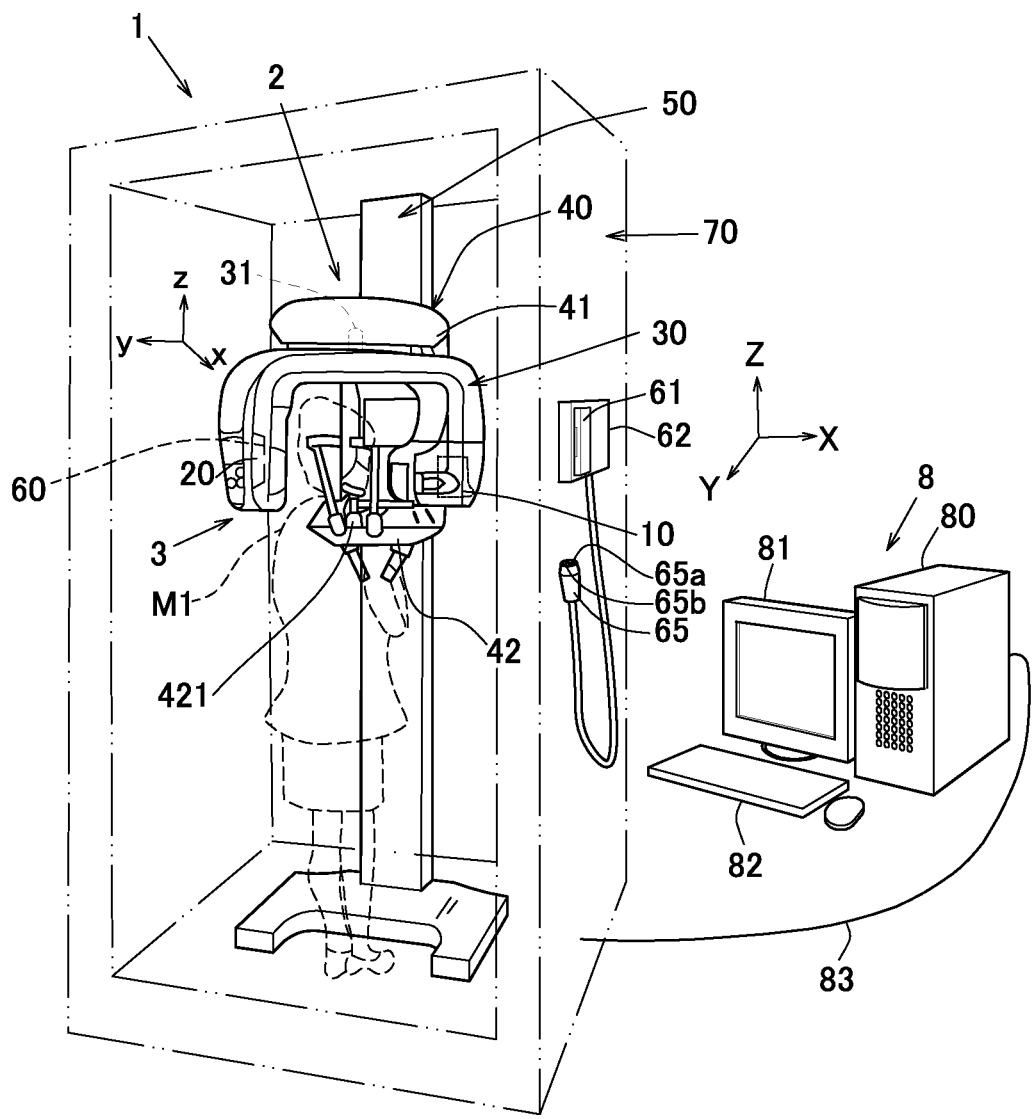
FIG. 1 is a schematic isometric view of an X-ray imaging device.
Figure 2:
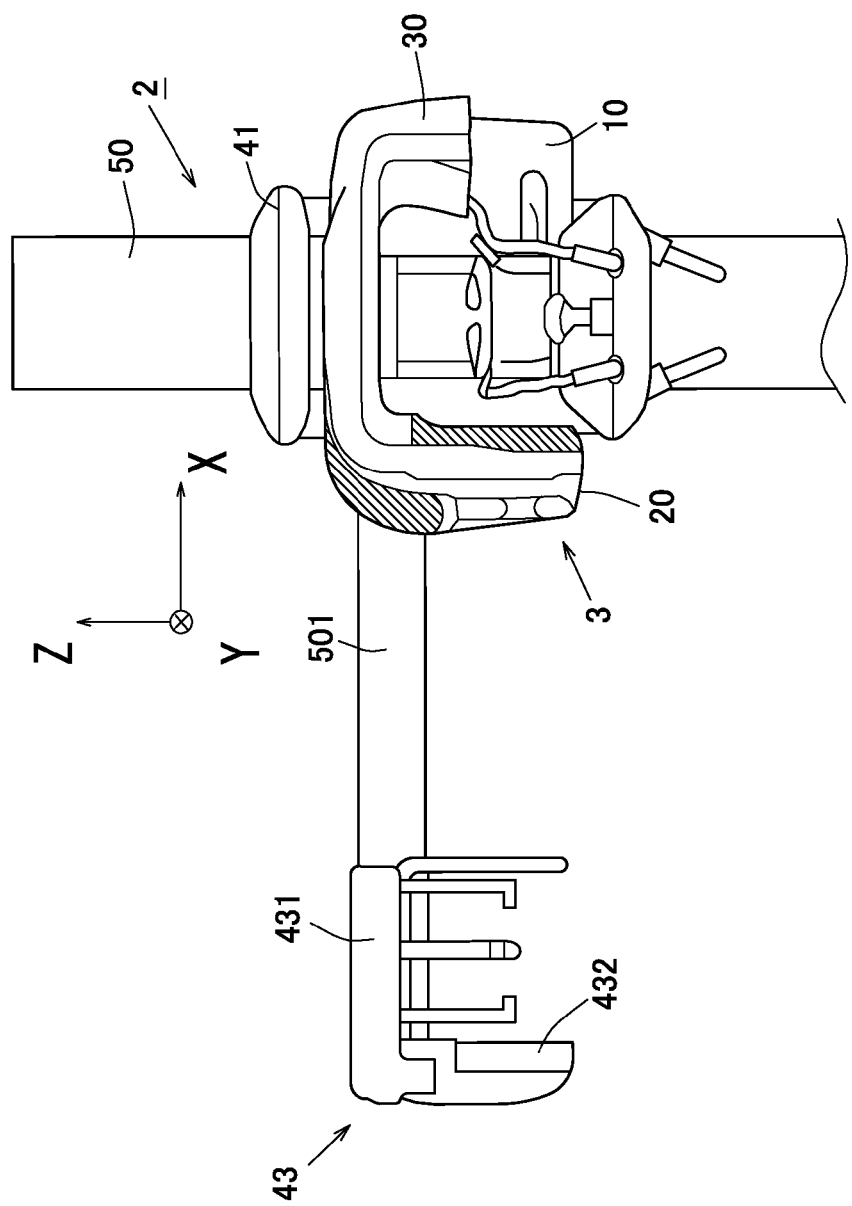
FIG. 2 is a partial front view of the X-ray imaging device in the state of including a cephalostat.
Figure 3:
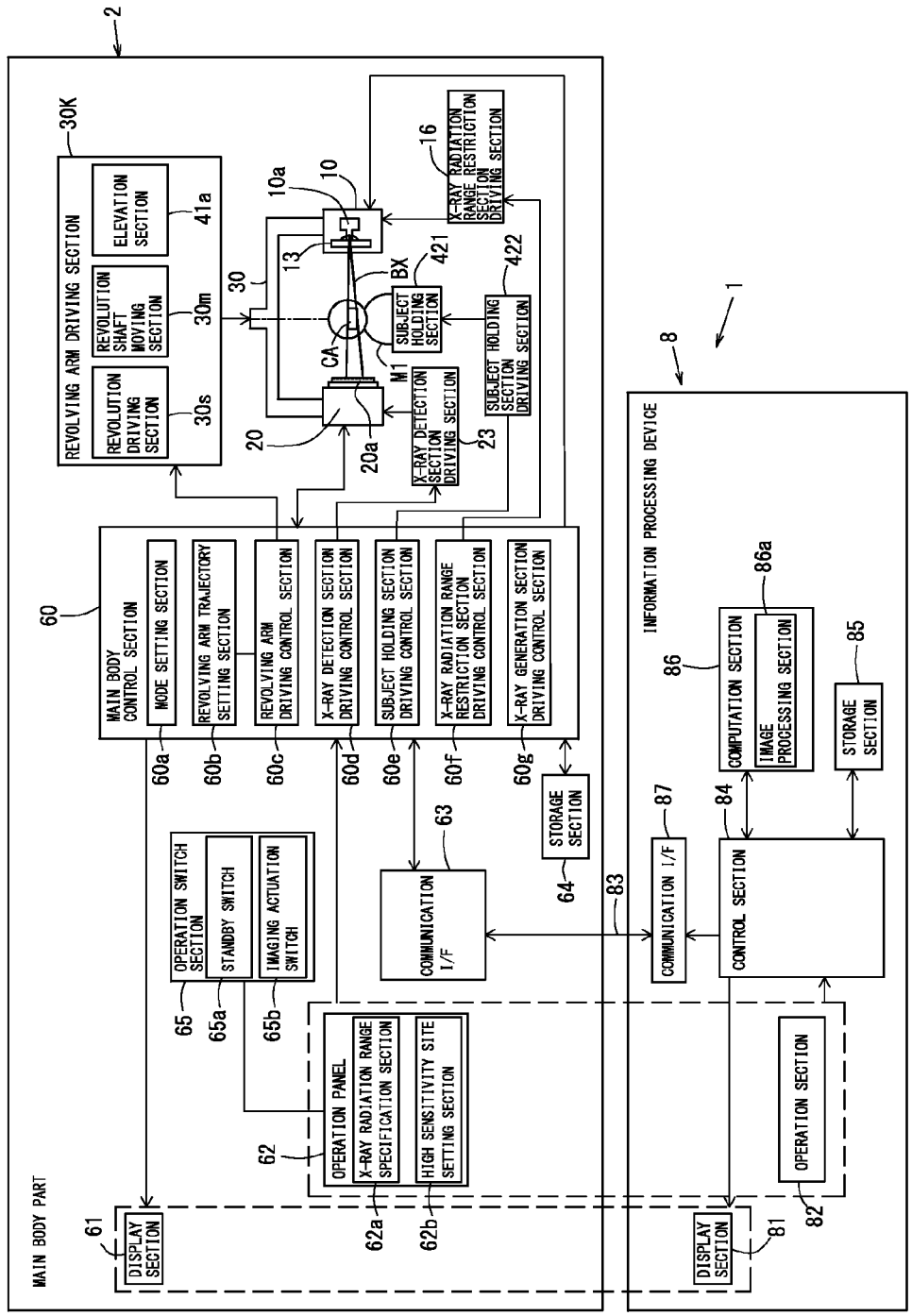
FIG. 3 is a block diagram showing a structure of the X-ray imaging device.
Figure 5A:
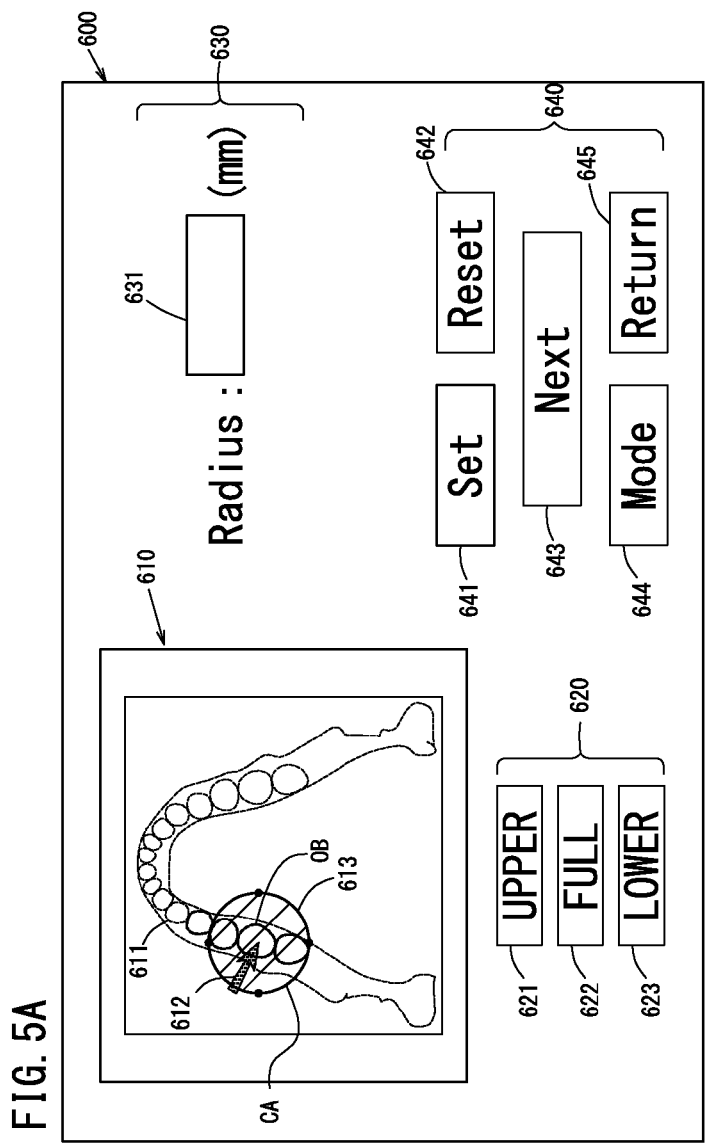
FIG. 5 is a schematic view showing a setting screen to set an imaging target site as a CT imaging area.

FIG. 1 is a schematic isometric view of an X-ray imaging device 1. FIG. 2 is a partial front view of the X-ray imaging device in the state of including a cephalostat 43. FIG. 3 is a block diagram showing a structure of the X-ray imaging device 1. FIG. 4 is a schematic isometric view of a beam formation mechanism 13. FIG. 5 is a schematic view of an imaging area setting screen 600 to set an imaging target site OB as a CT imaging area CA. In FIG. 5, the X-ray imaging device 1 is used for dental care, and the imaging target site OB includes the jaw bones. FIG. 6 is a schematic view of a high sensitivity site specification screen 700 to set a high sensitivity site H.

Figure 7:
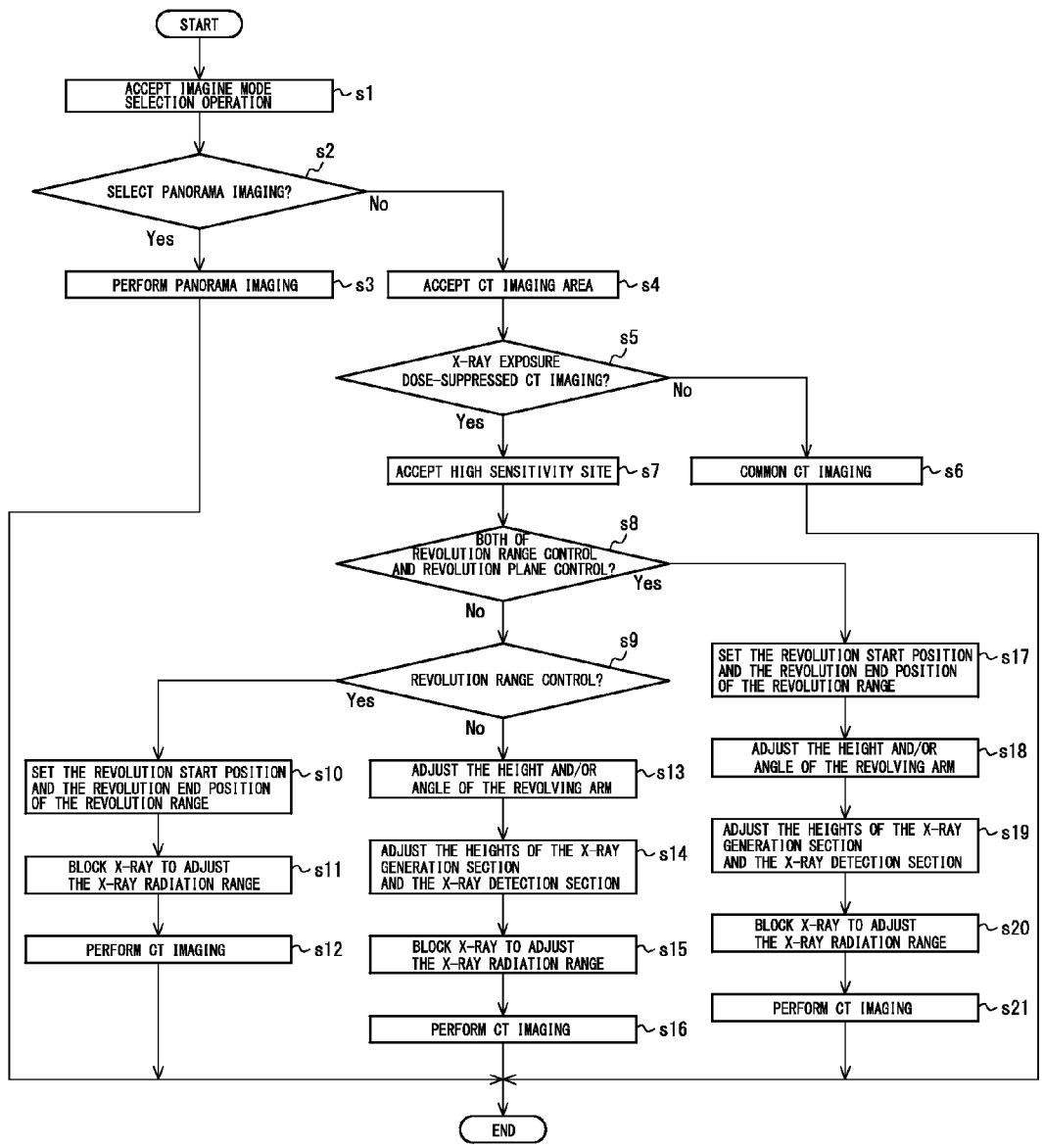
FIG. 7 is a flowchart showing a CT imaging process.
Figure 8:
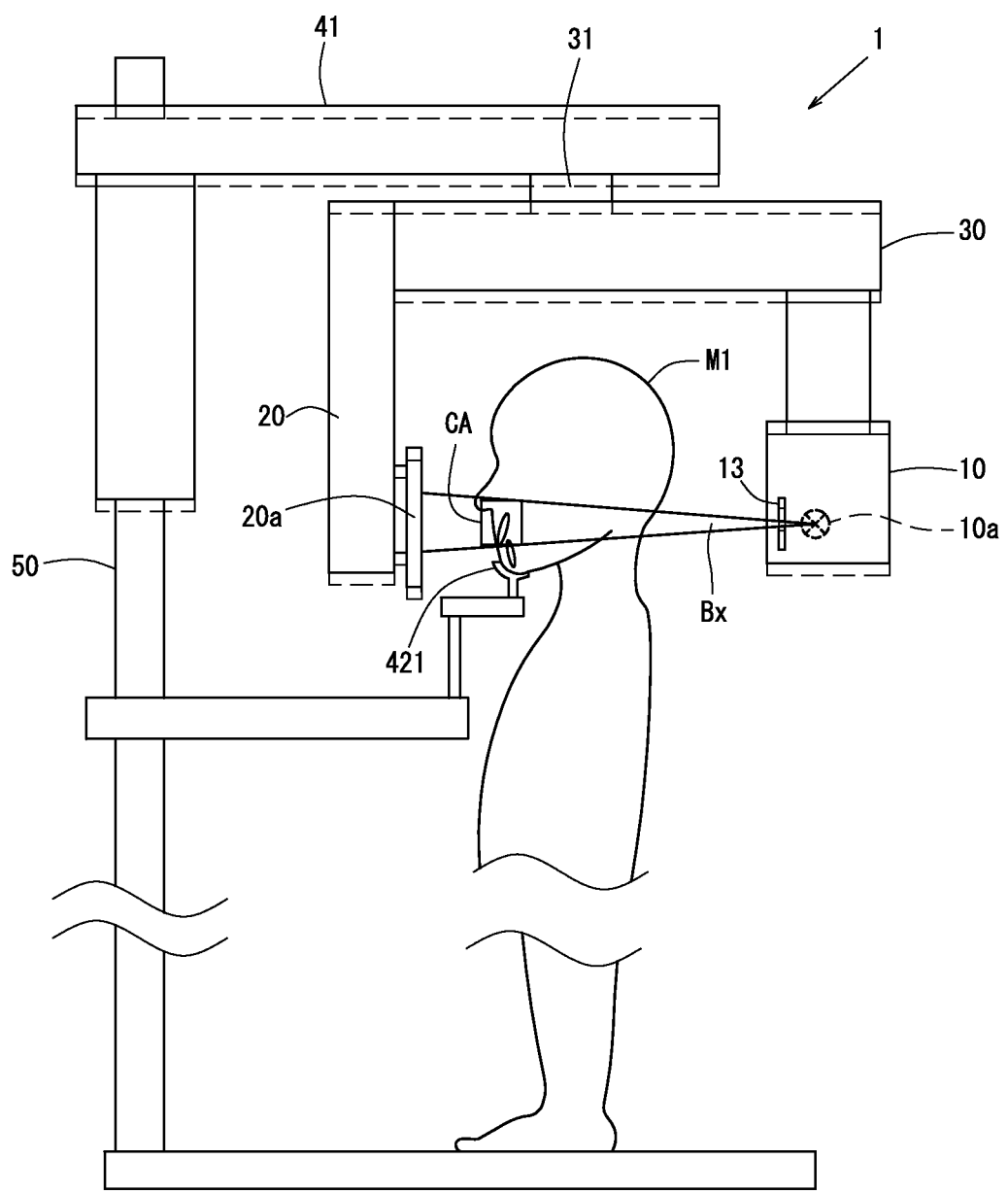
FIG. 8 is a schematic side view showing CT imaging performed on the upper jaw.
Figure 9:
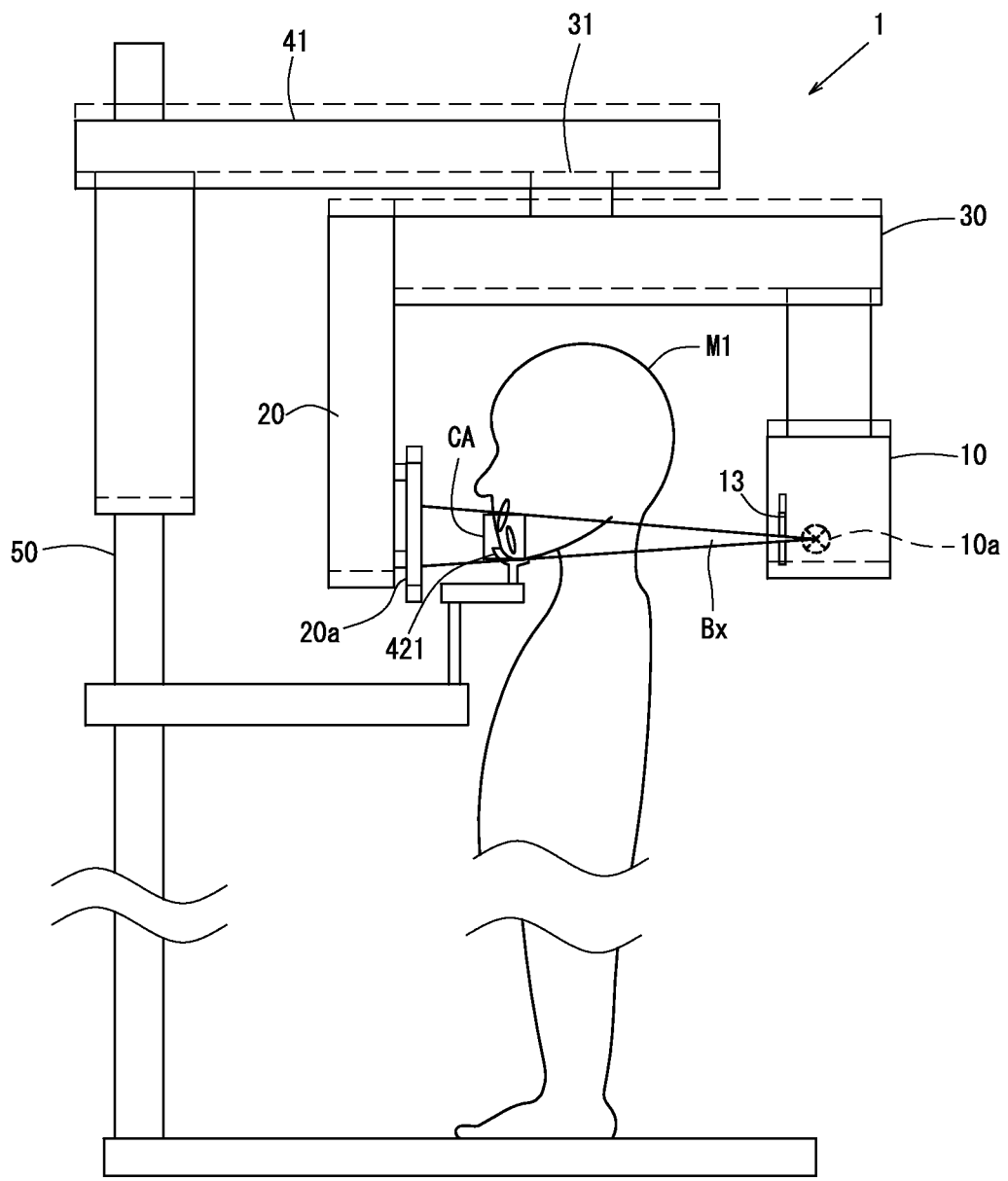
FIG. 9 is a schematic side view showing CT imaging performed on the lower jaw.
Figure 10:
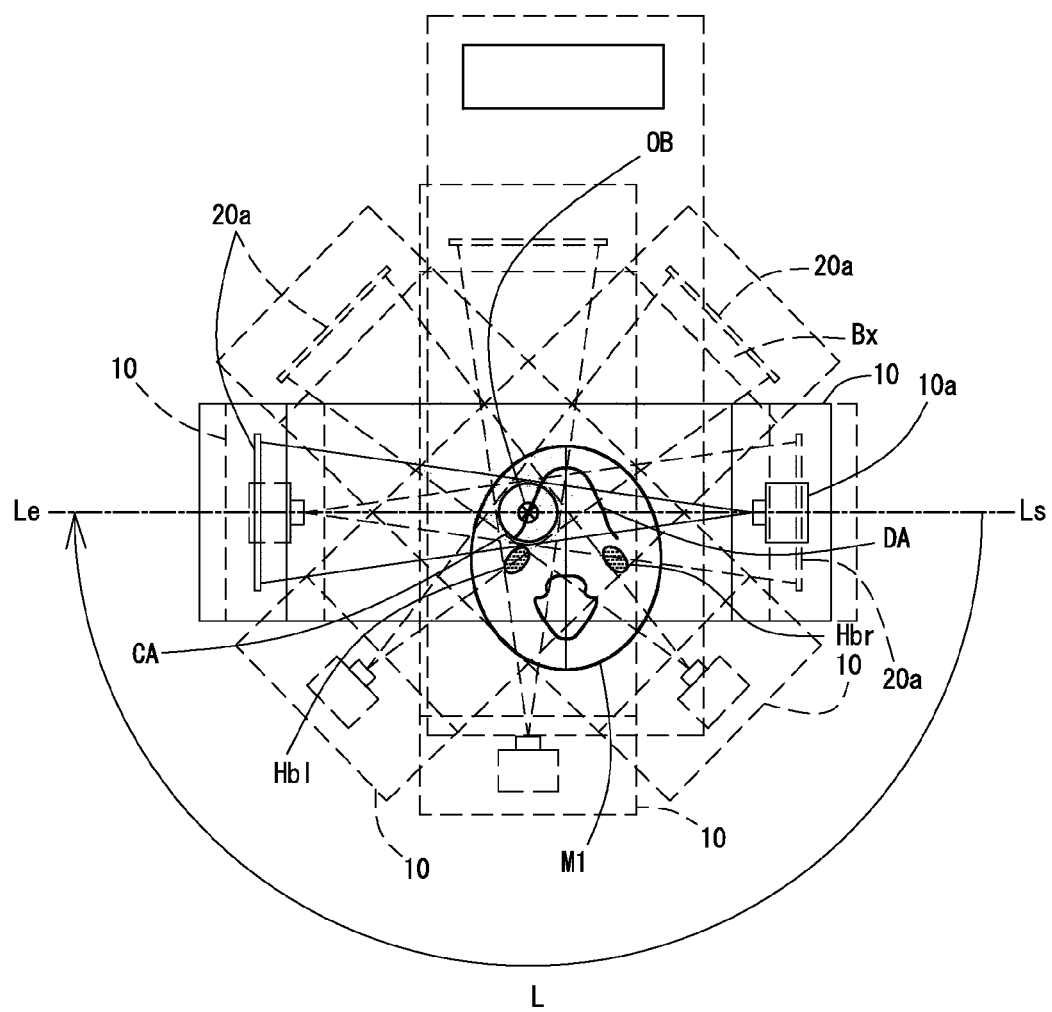
FIG. 10 is a schematic plan view showing common CT imaging performed with an X-ray cone beam revolving in a revolution range of 180 degrees.
Figure 11:
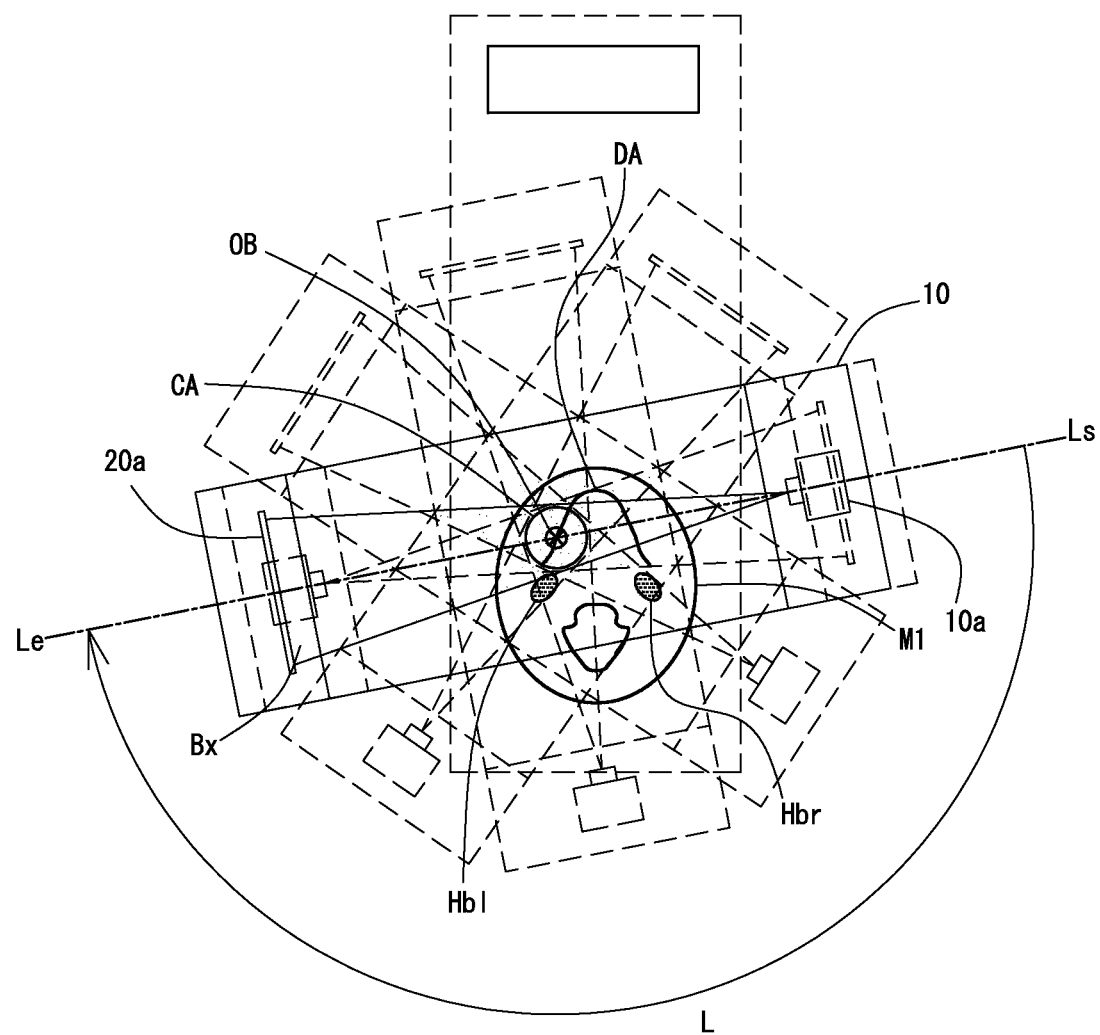
FIG. 11 is a schematic plan view showing exposure dose-suppressed CT imaging performed with the revolution range of the X-ray cone beam being controlled.
Figure 12:
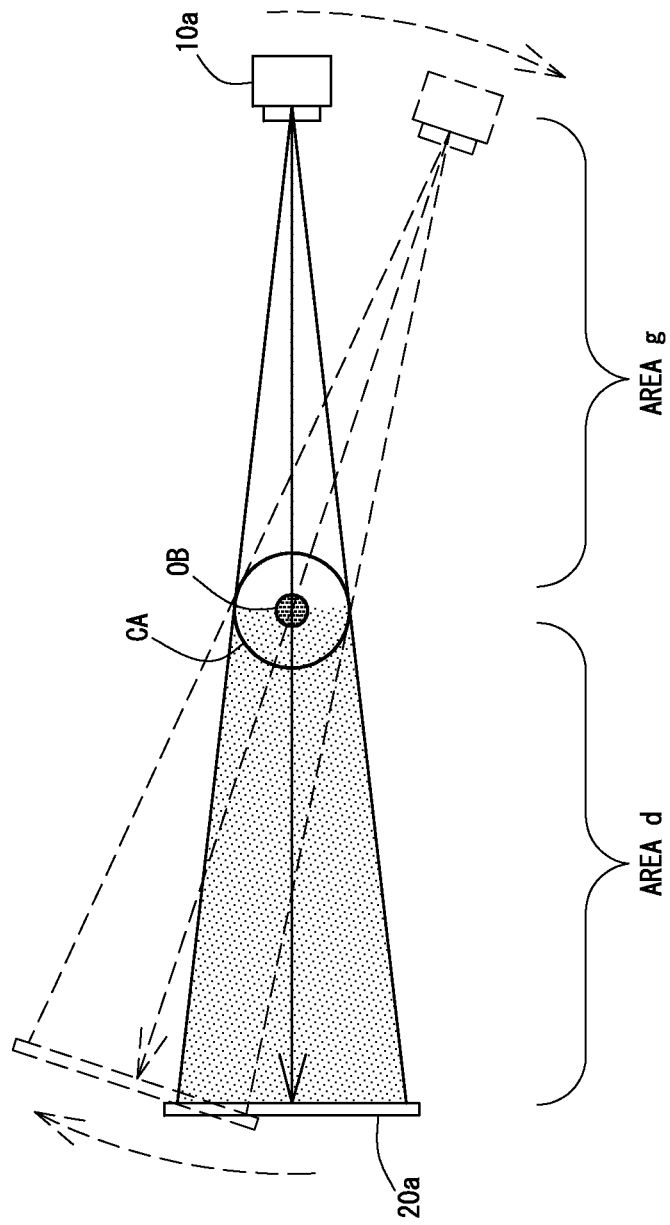
FIG. 12 is a schematic plan view of the X-ray cone beam.
Figure 13:
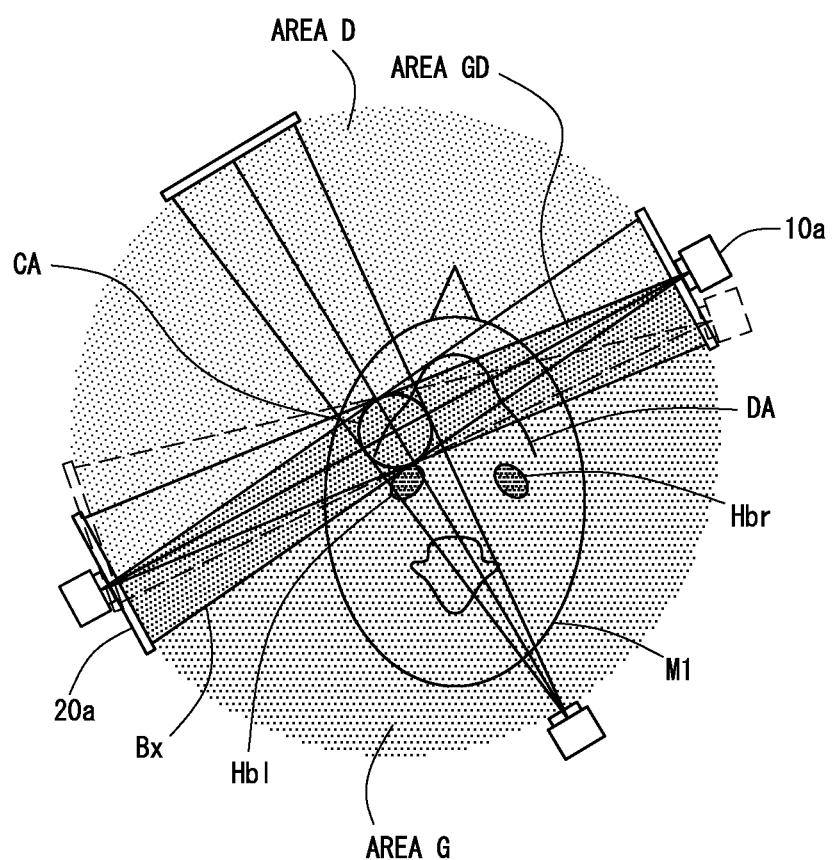
FIG. 13 is a schematic plan view showing a trajectory of the X-ray cone beam revolving in the revolution range of 180 degrees.

FIG. 7 is a flowchart showing a CT imaging process. FIG. 8 is a schematic side view showing CT imaging performed on the upper jaw. FIG. 9 is a schematic side view showing CT imaging performed on the lower jaw. FIG. 10 is a schematic plan view showing common CT imaging performed with an X-ray cone beam revolving in a revolution range of 180 degrees. FIG. 11 is a schematic plan view showing exposure dose-suppressed CT imaging performed with the revolution range of the X-ray cone beam being controlled. FIG. 12 is a schematic plan view of the X-ray cone beam. FIG. 13 is a schematic plan view showing a trajectory of the X-ray cone beam revolving in the revolution range of 180 degrees.

Figure 14:
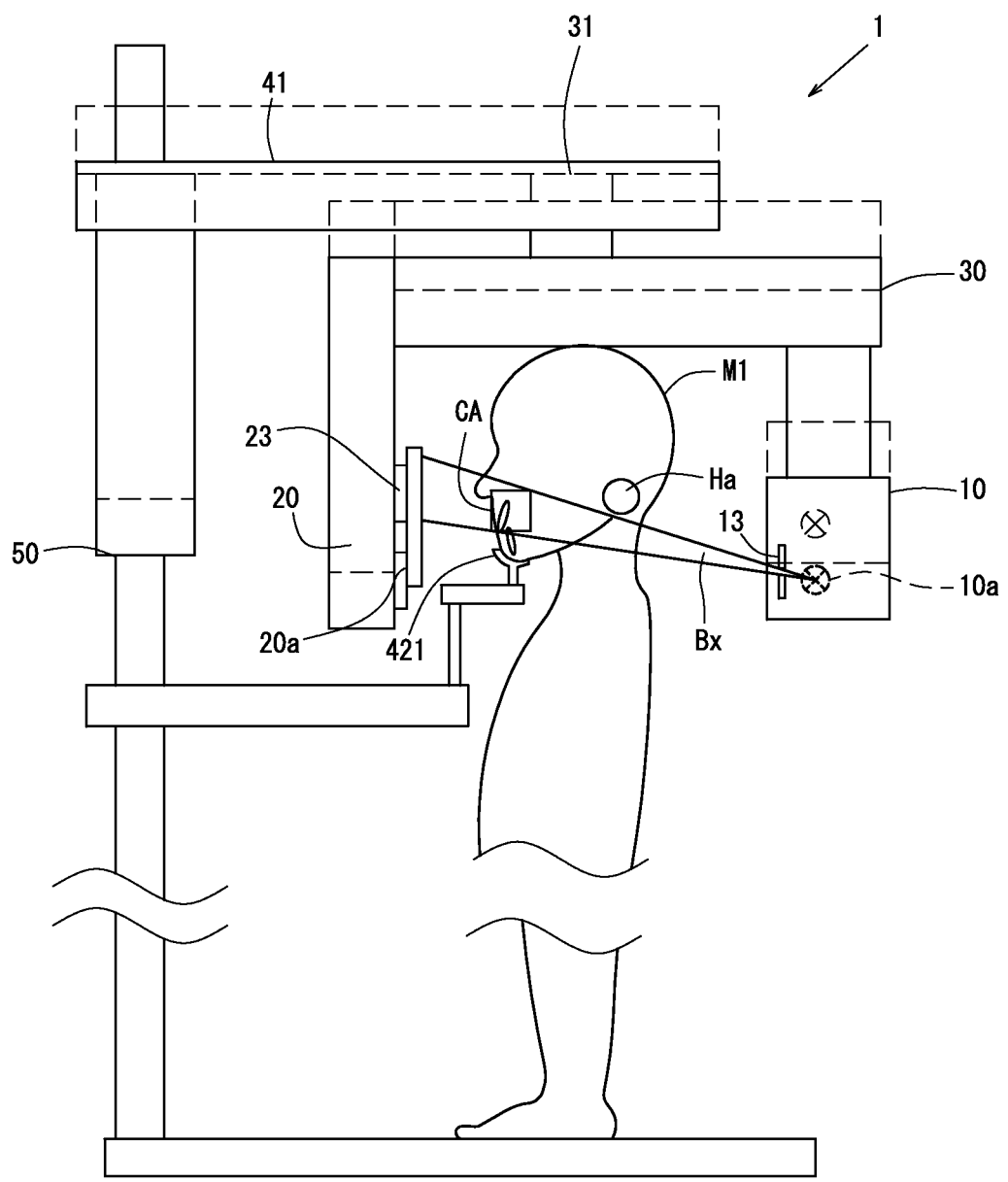
FIG. 14 is a schematic side view showing exposure dose-suppressed CT imaging performed on the upper jaw set as an imaging site, the CT imaging being performed by controlling the height and the radiation angle of the X-ray cone beam.
Figure 15:
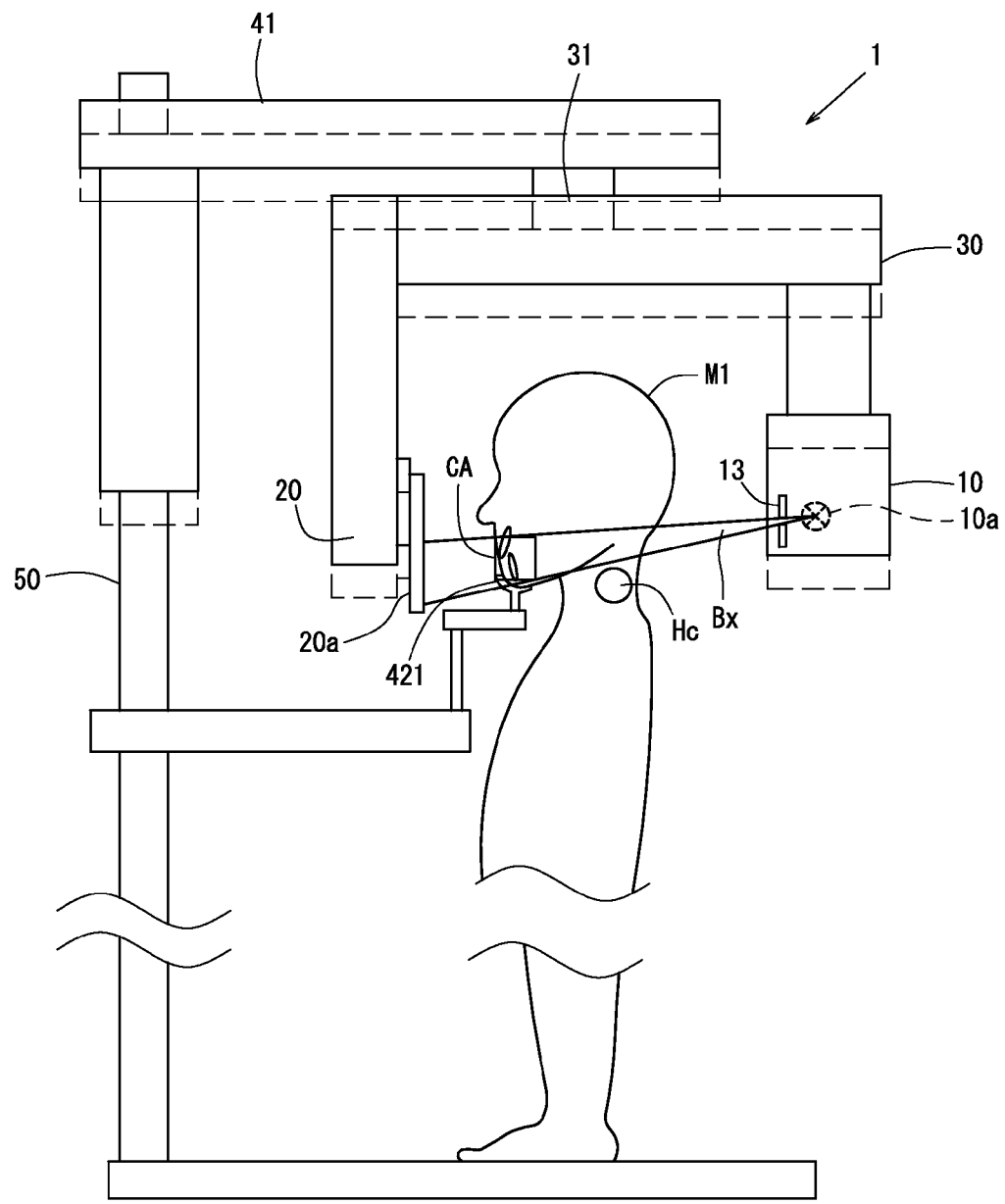
FIG. 15 is a schematic side view showing exposure dose-suppressed CT imaging performed on the lower jaw set as an imaging site, the CT imaging being performed by controlling the height and the radiation angle of the X-ray cone beam.
Figure 16:
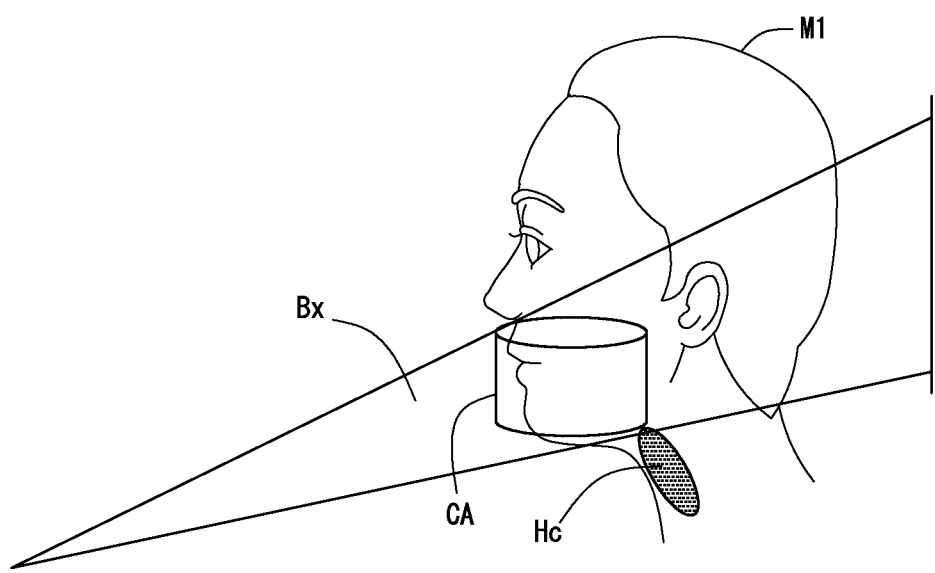
FIG. 16 is a schematic view showing exposure dose-suppressed CT imaging performed on the thyroid gland.
Figure 17A:
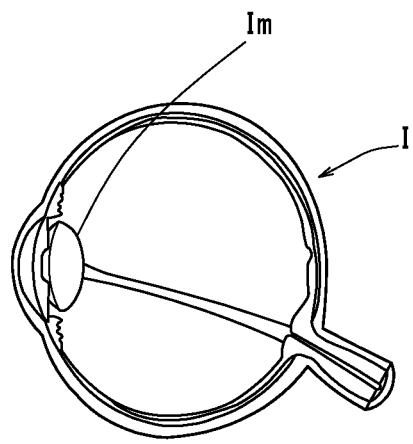
FIG. 17 shows exposure dose-suppressed CT imaging performed on the lens of the eyeball.
Figure 17B:
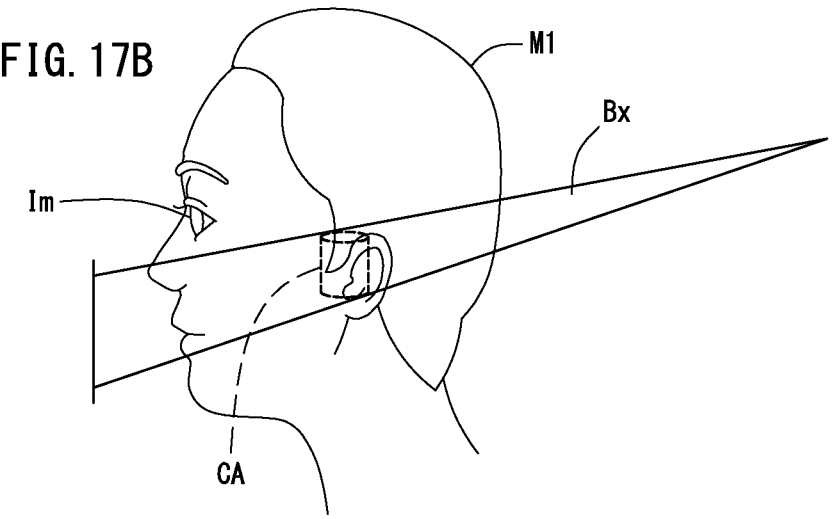
Figure 18:
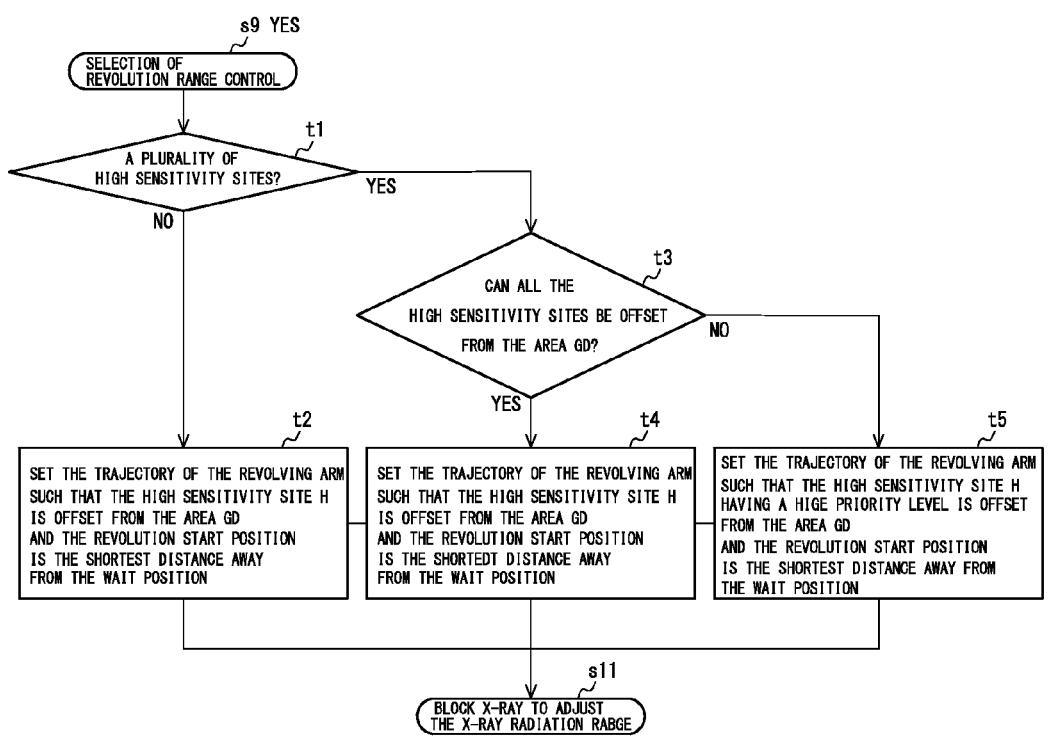
FIG. 18 is a flowchart showing exposure dose-suppressed CT imaging performed with the revolution range of the X-ray cone beam being controlled in the case where there are a plurality of high sensitivity sites.

FIG. 14 is a schematic side view showing exposure dose-suppressed CT imaging performed on the upper jaw set as an imaging site, the CT imaging being performed by controlling the height and the radiation angle of the X-ray cone beam. In this specification, the "height" refers to the level of an element in the Z-axis direction except for the body height of a subject M1 mentioned below. FIG. 15 is a schematic side view showing exposure dose-suppressed CT imaging performed on the lower jaw set as an imaging site, the CT imaging being performed by controlling the height and the radiation angle of the X-ray cone beam. FIG. 16 is a schematic view showing exposure dose-suppressed CT imaging performed on the thyroid gland. FIG. 17 shows exposure dose-suppressed CT imaging performed on the lens of the eyeball. FIG. 18 and the other figures will be specifically described later.

The X-ray imaging device 1 includes a main body part 2 that performs CT imaging to collect projection data and an information processing device 8 that processes the projection data collected by the main body part 2 to generate various types of images. The main body part 2 is preferably accommodated in a hollow parallelepiped X-ray-proof chamber 70, and is connected, via a connection table 83, to the information processing device 8 located outside the X-ray-proof chamber 70.

The main body part 2 includes an X-ray generation section 10 that emits an X-ray cone beam Bx formed of a flux of X-rays toward the subject M1 or an X-ray slit beam, an X-ray detection section detector 20 including an X-ray detector 20a that detects the X-ray cone beam Bx or an X-ray slit beam emitted by the X-ray generation section 10, a revolving arm 30 that supports the X-ray generation section 10 and the X-ray detection section 20, a support pillar 50 extending in a vertical direction, a revolving arm elevation section 40 which suspends the revolving arm 30 and is movable upward and downward in the vertical direction with respect to the support pillar 50, and a main body control section 60. The X-ray generation section 10, the X-ray detection section 20, and a beam formation mechanism 13 provided in the X-ray generation section 10 on the side facing the X-ray detection section 20 are included in an imaging mechanism 3.

The X-ray generation section 10 and the X-ray detection section 20 are suspended from, and fixed at, both of two ends of the revolving arm 30 respectively, and are supported so as to face each other. The revolving arm 30 is suspended from, and fixed to, the revolving arm elevation section 40 via a revolution shaft 31 extending in the vertical direction.

The revolving arm 30 is inverted U-shaped as seen in a front view and is revolvable about the revolution shaft 31 provided at a top end thereof. The revolution shaft 31 acts as a revolution center Sc. The X-ray generation section 10 and the X-ray detection section 20 are respectively attached to both of the two ends of the revolving arm 30. The revolving arm 30 is equipped with an X-ray detection section driving section 23 that moves the X-ray detection section 20, more specifically, the X-ray detector 20a, with respect to the revolving arm 30.

The X-ray detection section driving section 23 that moves the X-ray detection section 20, more specifically, the X-ray detector 20a, with respect to the revolving arm 30, may be any of various types of actuators, although not shown.

The X-ray detector 20a may be moved with respect to the revolving arm 30 as follows. For example, the X-ray detection section driving section 23 includes a roller fixed to a shaft of a motor which is fixed to a base part of the X-ray detection section driving section 23. Separately, a member that guides the X-ray detector 20a in a Z-axis direction is provided. The roller is put into contact with a rear surface of the X-ray detector 20a to move the X-ray detector 20a upward and downward via the member.

Alternatively, the X-ray detection section driving section 23 includes a male screw part pivotably fixed to the base part of the X-ray detection section driving section 23. Separately, a member that guides the X-ray detector 20a in the Z-axis direction and a female screw part fixed to the rear surface of the X-ray detector 20a are provided. The female screw part is moved upward and downward by the male screw part via the member to move the X-ray detector 20a upward and downward in the Z-axis direction using a motor as a driving source.

The revolving arm 30 is not limited to having the above-described shape. For example, the revolving arm 30 may include an annular part and rotate about the center thereof, and the X-ray generation section 10 and the X-ray detection section 20 may be supported by the revolving arm 30 so as to face each other.

Hereinafter, a direction parallel to an axial direction of the revolving shaft 31 (herein, the vertical direction) is defined as the "Z-axis direction", and a direction intersecting the Z-axis direction is defined as an "X-axis direction". A direction intersecting the X-axis direction and the Z-axis direction is defined as a "Y-axis direction". The X-axis direction and the Y-axis direction may be defined arbitrarily. Herein, where a test subject, namely, the subject M1, stands facing the support pillar 50 in the X-ray CT imaging device 1, the left-right direction for the subject M1 is defined as the "X-axis direction", and the front-rear direction for the subject M1 is defined as the "Y-axis direction". In this embodiment, the X-axis direction, the Y-axis direction and the Z-axis direction are perpendicular to each other. Hereinafter, the Z-axis direction may be referred to as the "vertical direction", and a direction in a plane defined by the X-axis direction and the Y-axis direction may be referred to as a "horizontal direction".

Regarding the X-axis direction, a rightward direction for the test subject is defined as a (+X) direction. Regarding the Y-axis direction, a rearward direction for the test subject is defined as a (+Y) direction. Regarding the Z-axis direction, the vertically upward direction for the test subject is defined as a (+Z) direction.

Regarding a three-dimensional coordinate system for the revolving arm 30, a direction in which the X-ray generation section 10 and the X-ray detection section 20 face each other is defined as a "y-axis direction", a horizontal direction perpendicular to the y-axis direction is defined as an "x-axis direction". A vertical direction perpendicular to the x-axis direction and the y-axis direction is defined as a "z-axis direction". In this embodiment, the Z-axis direction is the same as the z-axis direction. In this embodiment, the revolving arm 30 revolves about the revolution shaft 31, extending in the vertical direction, as the revolution axis. Therefore, the xyz Cartesian coordinate system rotates about the Z-axis (=z-axis) with respect to the XYZ Cartesian coordinate system.

Where the X-ray generation section 10 and the X-ray detection section 20 shown in FIG. 1 are seen in a plan view, a direction from the X-ray generation section 10 to the X-ray detection section 20 is defined as a "(+y) direction". A horizontal rightward direction perpendicular to the (+y) direction is defined as a "(+x) direction", and an upward direction in the vertical direction is defined as a "(+z) direction".

In the following description, an operation made by an operator may be occasionally included in a process of actuation of the device. This is based on the premise that an operation section of the device accepts an operation made by the operator.

The revolving arm elevation section 40 includes a top frame 41 and a bottom frame 42, and protrudes in a direction opposite to the side engageable with the support pillar 50 standing in the vertical direction, namely, protrudes in a front direction.

The top frame 41 includes a revolution shaft 31 to which the revolving arm 30 is attached, and a built-in elevation section 41*a*. The revolution shaft 31 attached to the revolving arm 30 is attached to the elevation section 41*a*. The elevation section 41*a* is movable in the vertical direction along the support pillar 50. Thus, the top frame 41 can move the revolving arm 30 upward and downward with respect to the support pillar 50.

The top frame 41 includes a revolution driving section 30*s* and a revolution shaft moving section 30*m*. The revolution driving section 30*s* includes a revolving motor (not shown) that revolves the revolving arm 30 about the revolution shaft 31 and a transmission mechanism (not shown) including a belt, a pulley, a rotation shaft and the like and passes the revolution shaft 31. The revolution driving section 30*s* transmits a rotation force of the revolving motor to the revolving arm 30 by the transmission mechanism to revolve the revolving arm 30. The revolution shaft moving section 30*m* moves the revolution shaft 31 in the x-axis direction and the y-axis direction with respect to the top frame 41.

The revolution shaft 31 and the revolving arm 30 have a bearing (not shown) therebetween so that the revolving arm 30 revolves smoothly about the revolution shaft 31.

The revolution shaft moving section 30*m* moves the revolution shaft 31 in the x-axis direction and the y-axis direction and thus can move the revolution center Sc. Therefore, the revolution shaft moving section 30*m* also acts as a revolution center moving section.

As disclosed in Japanese Laid-Open Patent Publication No. 2007-29168 and WO2009/063974 filed by the Applicant of the present application, the revolution shaft moving section 30*m* may be used to locate the revolution center Sc of the revolving arm 30 at a position different from the position of the center of the revolution shaft 31, which is a mechanical member that axially revolves the revolving arm 30. In this case, the revolution center Sc may be displaced in the x-axis direction and the y-axis direction.

In the example shown in the figures, the top frame 41 includes mechanical elements that drives the revolving arm 30, and acts as a revolving arm driving section 30K. The top frame 41 acting as the revolving arm driving section 30K drives the revolving arm 30 to drive the imaging mechanism 3, and thus also acts as an imaging mechanism driving section.

The revolving motor may be fixed inside the top frame 41, but alternatively may be fixed inside the revolving arm 30 so that a pivoting force acts on the revolution shaft 31. In this embodiment, the revolution shaft 31 extends in the vertical direction. Alternatively, the revolution shaft 31 may be inclined with respect to the vertical direction at an angle in a range including 90 degrees. Namely, the revolution shaft 31 may be perpendicular to the vertical direction.

In this embodiment, the revolution driving section 30*s* that revolves the revolving arm 30 includes the revolution shaft 31, the transmission mechanism including the bearing, the belt, the rotation shaft and the like, and the revolving motor, and revolves the revolving arm 30 about the revolution shaft 31, which is not rotated. The structure of revolving the revolving arm 30 is not limited to this.

For example, the revolution shaft 31 rotatably fixed to the revolving arm 30 may be rotated with respect to the top frame 41 so that the revolving arm 30 is revolved.

The bottom frame 42 is equipped with a subject holding section 421 including a head holder that fixes the subject M1 (in this example, the head of a human body) from left and right, a chin rest that fixes the chin or the like, and is also equipped with a subject holding section driving section 422 that moves the subject holding section 421. An ear rod including a part insertable into left and right earholes of the head of a human body may be used as the subject holding section 421.

In the case where the subject holding section 421 is a chin rest, the subject holding section driving section 422 may be, for example, an elevation actuator (not shown) that moves the chin rest upward and downward with respect to the bottom frame 42.

The elevation actuator that moves the chin rest upward and downward may have, for example, the following structure.

A screw shaft and a position adjusting motor similar to a length direction screw shaft 161*a* and a length direction position adjusting motor 162*a* described later with reference to FIG. 4 are fixed to the bottom frame 42. A screw groove similar to a screw groove 141 shown in FIG. 4 is fixed to the chin rest. The position adjusting motor is driven to rotate the screw shaft forward and rearward. As a result, the screw groove moves upward and downward in a length direction to move the chin rest upward and downward.

In the case where the CT imaging area CA has a width in the up-down direction that is equal to, or less than, the height of the teeth in the upper jaw or the teeth in the lower jaw, the elevation actuator is actuated to move the head of the subject M1 in accordance with whether the X-ray imaging target is the teeth in the upper jaw or the teeth in the lower jaw, so that the target site is encompassed in the CT imaging area CA.

In the case where the subject holding section 421 is a chair on which the subject M1 sits, the subject holding section driving section 422 may be, for example, an elevation actuator (not shown) that moves the chair upward and downward. Such an elevation actuator may be a larger version of the actuator that moves the chin rest upward and downward.

The elevation actuator is not limited to moving the chair in the Z-axis direction, but may move the chair in the X-axis direction or in the Y-axis direction by use of a known XY table or the like.

The revolving arm 30 is moved upward or downward by the revolving arm elevation section 40 in accordance with the body height of the subject M1 and is located at an appropriate position. In this state, the subject M1 is held by the subject holding section 421. In the example shown in FIG. 1, the subject holding section 421 holds the subject M1 such that the body axis of the subject M1 is in substantially the same direction as that of the axial direction of the revolution axis 31.

In the X-ray imaging device 1, one of the elevation section 41a and the subject holding section driving section 422 (especially, the mechanical element that moves the subject M1 upward and downward) may be omitted. Alternatively, both of the elevation section 41a and the subject holding section driving section 422 may be omitted. In this case, the top frame 41 or the subject holding section 421 is moved upward and downward manually.

The main body control section 60 controls the operation of each element of the main body part 2. As shown in FIG. 3, the main body control section 60 is located inside the main body part 2.

In more detail, the main body control section 60 is connected to the X-ray generation section 10, the X-ray detection section driving section 23, the revolving arm driving section 30K, the subject holding section driving section 422, an X-ray radiation range restriction section driving section 16, a display section 61, an operation panel 62 acting as an operation section, a communication interface 63 (hereinafter, referred to as the "communication I/F 63"), and a storage section 64. The main body control section 60 communicates with, and thus controls, each of these elements. The X-ray radiation range restriction section driving section 16, the surface section 61, the operation panel 62 acting as the operation section, the communication interface 63, and the storage section 64 will be described later.

The display section 61 may include a touch panel or the like so as to include apart of, or the entirety of, the functions of the operation section 62. In this case, the display section 61 also acts as the operation section 62.

The operation panel 62 is connected to an operation switch section 65. The operation switch section 65 includes a standby switch 65a, which is an operation switch that moves the revolving arm 30 to a revolution start position Ls when being pressed before start of CT imaging, and an imaging actuation switch 65b, which is an operation switch that directs the X-ray cone beam Bx toward the X-ray detection section 20 from the X-ray generation section 10 and revolving the revolving arm 30 to perform the CT imaging when being kept pressed.

The imaging actuation switch 65b may be a well-known switch conventionally referred to as a "dead man's switch". Alternatively, the imaging actuation switch 65b may also have a function of the standby switch 65a. In this case, the imaging actuation switch 65b moves the revolving arm 30 to the revolution start position Ls when being turned on for the first time, and keeps directing the X-ray beam Bx when being turned on for the second time (while being kept pressed).

The communication I/F 63 is connected to a connection cable 83 of an information processing main body part 80 to communicate with the information processing main body part 80. The storage section 64 stores, for example, information on the high sensitivity site H described later, and a control program usable by the main body control section 60 that controls each of the elements.

A default high sensitivity site H may be registered in terms of the position or range, or may be set to be registered or deleted by the operator. Alternatively, a default high sensitivity site H may be registered, and another high sensitivity site H may be newly registered or deleted by the operator. The portion that accepts a specification on a high sensitivity site H that includes the high sensitivity site specification section 700 is an example of high sensitivity site specification section. In the case where a default high sensitivity site H is registered, the portion that accepts the registration of the position and range thereof is another example of high sensitivity site specification section. The portion that stores the position and range of the registered high sensitivity site H is an element of the high sensitivity site specification section. In the structure that allows the operator to specify a high sensitivity site H each time, any site can be specified as the high sensitivity site H. In the structure that allows a default high sensitivity site H to be registered, the operator does not need to make a specification operation. Each structure has its own advantage.

The main body control section 60 connected to the elements described above uses the control program stored on the storage section 64 to act as a mode setting section 60a, a revolving arm trajectory setting section 60b and a revolving arm driving control section 60c that controls the revolving arm driving section 30K, an X-ray detection section driving control section 60d that controls the driving of the X-ray detection section driving section 23, a subject holding section driving control section 60e that controls the driving of the subject holding section driving section 422, an X-ray radiation range restriction section driving control section 60f that controls the driving of the X-ray radiation range restriction section driving section 16, or an X-ray generation section driving control section 60g that controls the driving of the X-ray generation section 10.

The revolving arm driving control section 60c controls a revolution range L of the revolving arm 30, and also performs control on the height of the revolving arm 30 and the setting of an X-ray revolution plane described later. The X-ray detection section driving control section 60d controls the height of the X-ray detection section by use of the X-ray detection section driving section 23 to perform control on the setting of the X-ray revolution plane and thus to perform control on the imaging of the X-ray detector 20a.

The X-ray radiation range restriction section driving control section 60f controls the height of an opening 17 of the beam formation mechanism 13 described later by use of the X-ray radiation range restriction section driving section 16 to perform control on the setting of the X-ray revolution plane. The X-ray generation section driving control section 60g controls the X-ray generation performed by an X-ray generator 10a included in the X-ray generation section 10.

The X-ray cone beam Bx is revolved while radiating, and therefore, forms a planar revolution trajectory having a certain thickness along with the revolution. A plane formed by such a revolution trajectory will be referred to as the "revolution plane".

The display section 61 including a liquid crystal monitor or the like that displays various types of information based on the control performed by the main body control section 60, and the operation panel 62 including buttons or the like that inputs various types of instructions to the main body control section 60, are attached to an outer wall of the X-ray-proof chamber 70 that accommodates the main body part 2.

The operation panel 62 has a function of an X-ray radiation range specification section 62a to specify the position or the like of an imaging area encompassing an imaging target site, namely, a CT imaging area CA, when displaying the imaging area setting screen 600 described later, and also has a function of a high sensitivity site setting section 62b to set a high sensitivity site H when displaying the high sensitivity site specification screen 700. The operation panel 62 is also usable for, for example, specifying the imaging area or the high sensitivity site H. The X-ray imaging may be performed in various modes. The operation panel 62 may be operated to select a mode.

The operation panel 62 may be provided in the main body part 2, or provided outside the outer wall of the X-ray-proof chamber 70 and also in the main body part 2.

The information processing device 8 includes the information processing main body part 80, a display section 81 including a display device such as, for example, a liquid crystal monitor, an operation section 82 including a keyboard, a mouse and the like, a control section 84, a storage section 85 that stores a control program usable by the control section 84 that controls each of the elements, a computation section 86, and a communication I/F 87.

The display section 81, the operation section 82, the storage section 85 and the computation section 86 are connected to the control section 84. The control section 84 uses the control program stored on the storage section 85 to control each of the elements. The computation section 86 uses an image processing program stored on the storage section 85 to act as an image processing section 86a.

An operator can input any of various instructions to the information processing device 8 having the above-described structure via the operation section 82. The display section 81 may include a touch panel. In this case, the display section 81 has a part of, or the entirety of, the functions of the operation section 82 and also acts as the operation section 82.

The display section 81 may display an image of various buttons or the like so that the buttons can be turned ON by an operation made on a pointer by a mouse or the like. In this case also, the display section 81 also acts as the operation section 82.

The information processing device 80 may be, for example, a computer, a work station or the like, and can transmit and receive various types of data with the main body part 2 via the communication I/F 87 by the connection cable 83, which is a communication cable. The communication between the main body part 2 and the information processing device 8 may be performed wirelessly.

The information processing device 8 processes projection data acquired by the main body part 2 by use of the image processing section 86a of the computation section 86 to re-construct three-dimensional data (volume data) represented by voxels. For example, the information processing device 8 can set a specific plane in the three-dimensional data, and re-construct a tomographic image of the specific plane.

Now, with reference to FIG. 4, the beam formation mechanism 13 provided in the X-ray generation section 10 will be described. The beam formation mechanism 13 partially blocks the X-ray generated by the X-ray generator 10a to restrict a radiation range thereof, such that the X-ray cone beam Bx directed toward the X-ray detection section 20 has a conical shape. In this specification, the term "conical shape" encompasses the conical shape in the generally used sense and also a pyramid shape.

The X-ray generation section 10 suspended from the revolving arm 30 so as to face the X-ray detection section 20 includes the X-ray generator 10a accommodated in a housing 11, and the X-ray generator 10a includes an X-ray tube. In a front surface of the housing 11, an output opening 12 that transmits the X-ray generated in the X-ray generator 10a accommodated in the housing 11 is formed. Forward to the output opening 12 (toward the viewer of FIG. 4, and in the y-axis direction from the X-ray generation section 10, more specifically, in the +y direction from the X-ray generation section 10), the beam formation mechanism 13 is provided.

The beam formation mechanism 13 includes length direction X-ray radiation restriction sections 14 (14a, 14b) that block the X-ray in a length direction of the radiation range (z-axis direction), lateral direction X-ray radiation restriction sections 15 (15a, 15b) that block the X-ray in a lateral direction of the radiation range (x-axis direction), and the X-ray radiation range restriction section driving section 16 (16a and 16b) that moves the length direction X-ray radiation restriction sections 14 and the lateral direction X-ray radiation restriction sections 15.

The length direction X-ray radiation restriction sections 14 include an upper length direction X-ray radiation restriction section 14a and a lower length direction X-ray radiation restriction section 14b which are longer in the lateral direction and are respectively located above and below the output opening 12 as seen in a front view. The lateral direction X-ray radiation restriction sections 15 include a left lateral direction X-ray radiation restriction section 15a and a right lateral direction X-ray radiation restriction section 15b which are longer in the length direction and are respectively located to the left and to the right of the output opening 12 as seen in a front view.

In FIG. 4, the lateral direction X-ray radiation restriction sections 15 are located on the X-ray generation section 10 side with respect to the length direction X-ray radiation restriction sections 14. Alternatively, the length direction X-ray radiation restriction sections 14 may be located on the X-ray generation section 10 side with respect to the lateral direction X-ray radiation restriction sections 15.

The X-ray radiation range restriction section driving section 16 includes blocking plate length direction moving mechanisms 16a and blocking plate lateral direction moving mechanisms 16b. The blocking plate length direction moving mechanisms 16a respectively move the two length direction X-ray radiation restriction sections 14a and 14b, which are two blocking plates, in the length direction. The blocking plate lateral direction moving mechanisms 16b respectively move the two lateral direction X-ray radiation restriction sections 15a and 15b, which are two blocking plates, in the lateral direction.

Each blocking plate length direction moving mechanism 16a acts as follows. The length direction screw shaft 161a which is in screw engagement with the screw groove 141 (to-be-guided member having a female thread in an inner surface thereof), attached to the length direction X-ray radiation restriction section 14 along the length direction screw shaft 161a, is rotated by the length direction positional adjustment motor 162a (162), and thus each length direction X-ray radiation restriction section 14 is moved in the length direction.

One of the blocking plate length direction moving mechanisms 16a is located at an upper position in correspondence with the upper length direction X-ray radiation restriction section 14a, and the other blocking plate length direction moving mechanism 16a is located at a lower position in correspondence with the lower length direction X-ray radiation restriction section 14b. Therefore, the upper length direction X-ray radiation restriction section 14a and the lower length direction X-ray radiation restriction section 14b can move in the length direction independently from each other.

The blocking plate length direction moving mechanisms 16a are located offset in the lateral direction from the lateral-direction center of the length direction X-ray radiation restriction sections 14 which are longer in the lateral direction. At a position offset in the lateral direction from the lateral-direction center of the length direction X-ray radiation restriction sections 14 in the opposite direction, an inclination restriction shaft 143 is provided. The inclination restriction shaft 143 is inserted through inclination restriction holes 142 (to-be-guided members each having a length direction through-hole) in correspondence with the upper length direction X-ray radiation restriction section 14a and the lower length direction X-ray radiation restriction section 14b. Therefore, the length direction X-ray radiation restriction sections 14 can be moved in the length direction by the blocking plate length direction moving mechanisms 16a without being inclined.

Each blocking plate lateral direction moving mechanism 16b acts as follows. A lateral direction screw shaft 161b which is in screw engagement with a screw groove 161 (to-be-guided member having a female thread in an inner surface thereof), attached to the lateral direction X-ray radiation restriction section 15 along the lateral direction screw shaft 161b, is rotated by the length direction positional adjustment motor 162a (162), and thus each lateral direction X-ray radiation restriction section 15 is moved in the lateral direction.

One of the blocking plate lateral direction moving mechanisms 16b is located at a left position in correspondence with the left lateral direction X-ray radiation restriction section 15a, and the other blocking plate lateral direction moving mechanism 16b is located at a right position in correspondence with the right lateral direction X-ray radiation restriction section 15b. Therefore, the left lateral direction X-ray radiation restriction section 15a and the right lateral direction X-ray radiation restriction section 15b can move in the lateral direction independent from each other.

The blocking plate lateral direction moving mechanisms 16b are located offset in the length direction from the length-direction center of the lateral direction X-ray radiation restriction sections 15 which are longer in the length direction. At a position offset in the length direction from the length-direction center of the lateral direction X-ray radiation restriction sections 15 in the opposite direction, an inclination restriction shaft 153 is provided. The inclination restriction shaft 153 is inserted through inclination restriction holes 152 (to-be-guided members each having a lateral direction through-hole) in correspondence with the left lateral direction X-ray radiation restriction section 15a and the right lateral direction X-ray radiation restriction section 15b. Therefore, the lateral direction X-ray radiation restriction sections 15 can be moved in the lateral direction by the blocking plate lateral direction moving mechanisms 16b without being inclined.

The length direction position adjusting motor 162a and a lateral direction position adjusting motor 162b are each a positional adjustment motor 162 and also a blocking driving source of the beam formation mechanism 13.

The length direction X-ray radiation restriction sections 14 and the lateral direction X-ray radiation restriction sections 15 are included in an X-ray radiation range restriction section 13A.

As described above, the beam formation mechanism 13 includes the length direction X-ray radiation restriction sections 14, the lateral direction X-ray radiation restriction sections 15 and the X-ray radiation range restriction section driving sections 16, and is located forward with respect to the output opening 12 of the X-ray generation section 10. Owing to this, the X-ray generated by the X-ray generation section 10 is partially blocked to restrict the X-ray radiation range thereof, and thus the X-ray cone beam Bx directed toward the X-ray detection section 20 has a conical shape.

This will be described in more detail. The distance between edges 14c, facing each other, of the upper length direction X-ray radiation restriction section 14a and the lower length direction X-ray radiation restriction section 14b is adjusted by the blocking plate length direction moving mechanisms 16a, and the distance between edges 15c, facing each other, of the left lateral direction X-ray radiation restriction section 15a and the right lateral direction X-ray radiation restriction section 15b is adjusted by the blocking plate lateral direction moving mechanisms 16b. Thus, an opening 17 having a square shape as seen in a front view that forms the X-ray cone beam having a desired shape can be defined by the edges 14c and the edges 15c.

The beam formation mechanism 13 having such a structure restricts the radiation range of the X-ray cone beam Bx, generated by the X-ray generator 10a, when the X-ray cone beam Bx passes the opening 17 formed by the X-ray cone beam Bx 13A. As described above, the X-ray radiation range restriction section driving section 16 is connected to the main body control section 60, and can restrict the radiation range of the X-ray beam Bx to a desired range by use of the X-ray radiation range restriction section driving control section 60f.

The X-ray cone beam Bx is not limited to having a conical shape.

For example, the number of the X-ray radiation restriction sections may be increased so that the X-ray cone beam Bx has a cross-section perpendicular to the radiation axis thereof that is pentagonal or of a polygonal shape having more than five sides. Alternatively, the structure of a diaphragm of a well-known camera that performs visible light imaging may be adopted to block the X-ray such that the X-ray beam Bx has a cross-section perpendicular to the radiation axis thereof that is of a circular shape having a variable diameter. In this case, the three-dimensional shape of the X-ray CT imaging area may be spherical.

The X-ray imaging device 1 may include the cephalostat 43 as shown in FIG. 2. This will be described in more detail. The cephalostat 43 is attached to, for example, an arm 501 extending horizontally from an intermediate position of the support pillar 50. The cephalostat 43 includes a fixing tool 431 that fixes the head of a human body at a fixed position and an X-ray detector 432 usable for cephalo imaging. The cephalostat 43 may be a cephalostat disclosed in Japanese Laid-Open Patent Publication No. 2003-245277 or any of various types of cephalostats.

Now, the imaging area setting screen 600 displayed as the X-ray radiation range specification section 62a on the operation panel 62 will be described. As shown in FIG. 5, the imaging area setting screen 600 is a screen to set a CT imaging area CA encompassing an imaging target site OB. The imaging area setting screen 600 includes an image display section 610 that displays a dental arch image 611, an upper/lower jaw selection section 620, a selection range setting section 630, and a condition setting section 640.

The CT imaging area CA as seen in the Z-axis direction can be set to have a shape covering a part of the dental arch.

The shape covering a part of the dental arch DA can be set to have any range in accordance with the purpose of imaging the teeth included in the dental arch DA or jaw bone. For example, as shown in FIG. 5(a), the CT imaging area CA may have a perfectly circular shape.

Figure 5B:
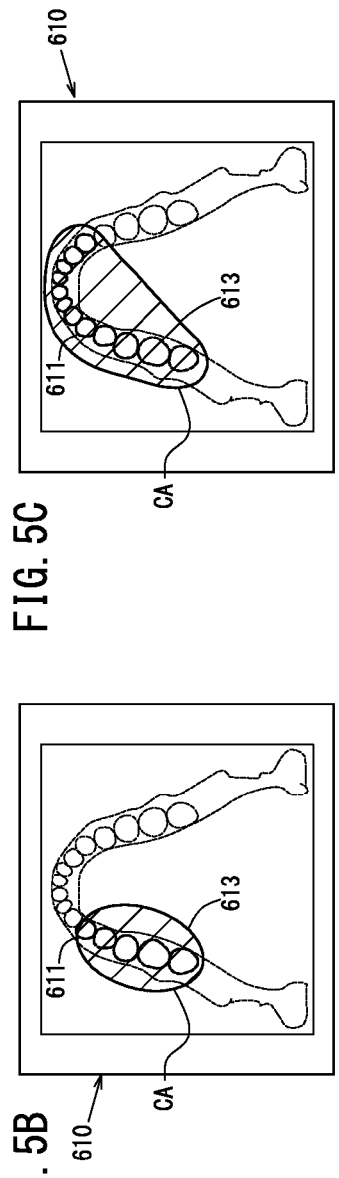
Figure 6:
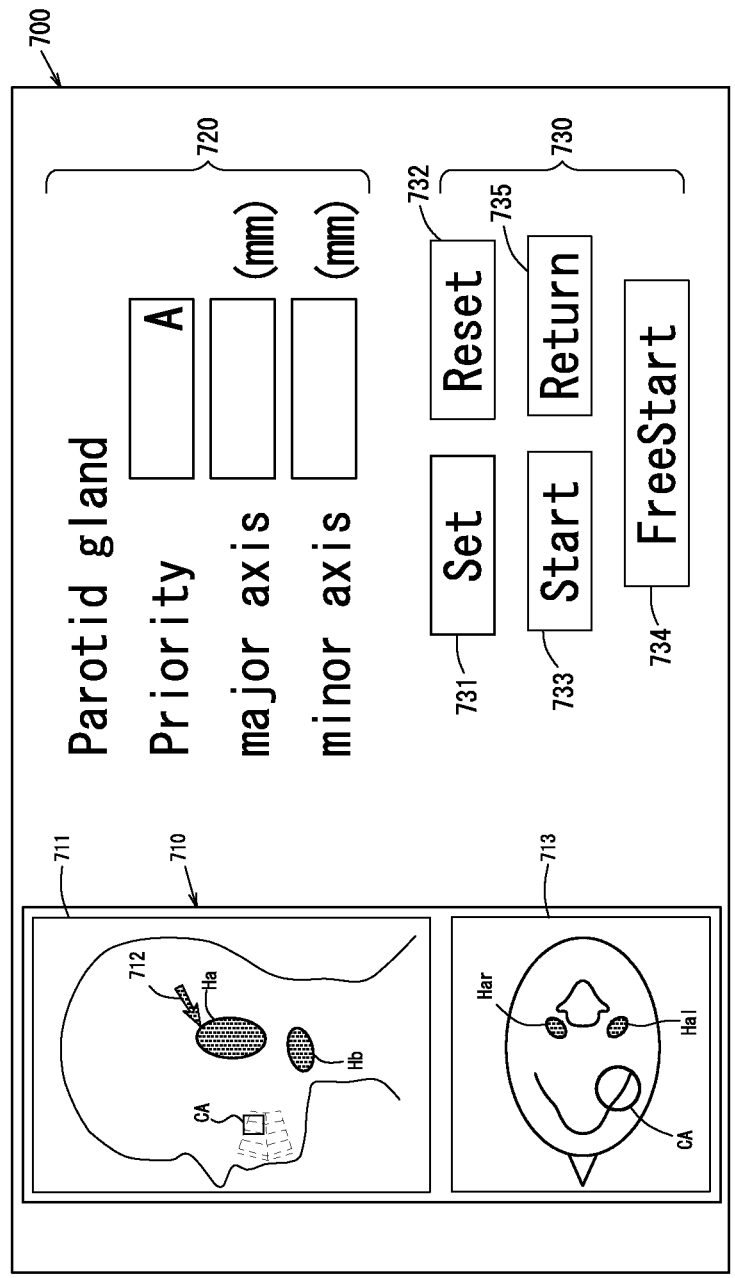
FIG. 6 is a schematic view of a setting screen to set a high sensitivity site.

Alternatively, as shown in FIG. 5(b), the CT imaging area CA may have an elliptical shape.

A perfectly circular CT imaging area CA and an elliptical CT imaging area CA are both suitable to perform CT imaging on a local imaging target site in the dental arch DA. A perfectly circular CT imaging area CA has an advantage of simplifying the mechanical control performed by the imaging mechanism 3 during the CT imaging. In the case where the imaging target site has a lengthy shape extending along a curved part of the dental arch DA, an elliptical CT imaging area CA has an advantage of suppressing the X-ray exposure dose of the subject M1 to a necessary but minimum possible level.

In the case where, for example, the imaging target site encompasses about four or less molar teeth, preferably about three or less molar teeth, a perfectly circular CT imaging area CA suppresses the unnecessary X-ray exposure dose to an extremely low level because the area encompassed by the CT imaging area CA other than the teeth is small.

The CT imaging area CA may have a shape shown in FIG. 5 (c).

Figure 5C:
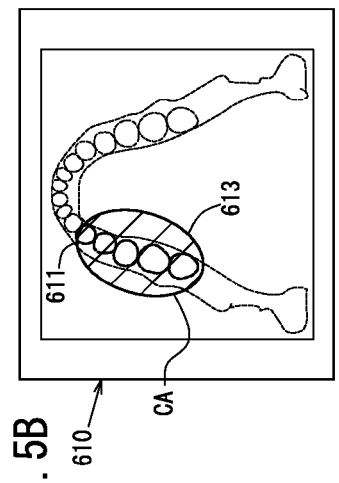

In FIG. 5(c), the profile of the CT imaging area has an outer part which is curved along a curved part of the dental arch DA and a straight or generally straight inner part which connects both of two ends of the curved outer part.

The CT imaging area CA having such a shape suppresses the X-ray exposure dose of the subject M1 to a necessary but minimum possible level.

In the case where the CT imaging area CA has the shape shown in FIG. 5(b) or FIG. 5(c), the lateral direction X-ray radiation restriction sections 15 (15a, 15b) are driven during the CT imaging to adapt the width of the X-ray cone beam Bx in the x-axis direction to the width of the CT imaging area CA in accordance with the revolving angle of the revolving arm 30.

The X-ray imaging device 1 may perform CT imaging with on the CT imaging area CA of only one of the shapes shown in FIG. 5(a) through FIG. 5(c). Alternatively, the X-ray imaging device 1 may perform CT imaging on the CT imaging area CA of all the shapes shown in FIG. 5(a) through FIG. 5(c) so that one of the shapes can be selected by mode switching.

In FIG. 5(a), the image display section 610 displays a specification cursor (pointer) 612 that specifies the center of the CT imaging area CA and a CT imaging area line 613 that defines a perfect circle having the center specified by the specification cursor 612 and a radius specified by the selection range setting section 630 described later. The specification cursor 612 and the CT imaging area line 613 are displayed as overlapping the dental arch image 611.

The upper/lower jaw selection section 620 includes an UPPER button 621 to set the CT imaging area CA on the upper jaw, a FULL button 622 to set the CT imaging area CA on both of the upper jaw and the lower jaw, and a LOWER button 623 to set the CT imaging area CA on the lower jaw.

The selection range setting section 630 includes a text box 631 usable to input a radius from the center specified by the specification cursor 612. Alternatively, the selection range setting section 630 may be usable to input a diameter.

The condition setting section 640 includes a Set button 641, a Reset button 642, a Next button 643, a Mode button 644, and a Return button 645.

The Set button 641 is an operation button to save the settings on the CT imaging area CA made by the image display section 610, the upper/lower jaw selection section 620 and the selection range setting section 630 (for performing a setting operation accepting step s12).

The Reset button 642 is an operation button to reset the settings on the CT imaging area CA made by the image display section 610, the upper/lower jaw selection section 620 and the selection range setting section 630.

The Next button 643 is an operation button to change the imaging area setting screen 600 to the high sensitivity site specification screen 700 to set a high sensitivity area H described later based on the settings saved by the Set button 641.

The Mode button 644 is an operation button to select any of various modes. More specifically, the Mode button 644 is usable to switch a perfect circle mode to set the CT imaging area CA to a perfect circle to an ellipse mode to set the CT imaging area CA to an ellipse or vice versa, or that selects a panorama mode to perform panorama imaging.

The "panorama imaging" refers to panorama X-ray imaging. The panorama image obtained by the panorama X-ray imaging is a panorama X-ray image.

The Return button 645 is an operation button to return the imaging area setting screen 600 to an initial screen (not shown).

The display section 61 acts as an operation display section. When CT imaging is to be performed on an imaging target site, first, the imaging area setting screen 600 provided on the display section 61 accepts an operation of setting the CT imaging area line 613 encompassing the imaging target site OB.

This will be described in more detail. One of the buttons in the upper/lower jaw selection section 620 is pressed to indicate whether the imaging target site OB is in the upper jaw, the lower jaw or both of the upper jaw and the lower jaw. The specification cursor 612 is operated on the dental arch image 611 shown in the image display section 610 of the imaging area setting screen 600 to specify the center of a circle defining the CT imaging area CA. A value of the radius of the circle is input to the text box 631 of the selection range setting section 630.

Specification operation information, based on the center of the circle defining the CT imaging area CA which is input to the imaging area setting screen 600 and the value of the radius which is input to the text box 631, is transmitted to the information processing device 8. Upon receipt of the specification operation information, the information processing device 8 transmits the information on the CT imaging area line 613 to the operation display section 61. Upon receipt of the information on the CT imaging area line 613, the operation display section 61 displays the CT imaging area line 613 based on the received information as overlapping the dental arch image 611 in the image display section 610 of the imaging area setting screen 600.

Upon checking the imaging area setting screen 600, the operator confirms that the CT imaging area line 613 is set to a desired position and a desired range on the dental arch image 611. When the Set button 641 is pressed, the CT imaging area line 613 is transmitted as a circle defining the CT imaging area CA to the information processing device 8. When the Next button 643 is pressed, the imaging area setting screen 600 is changed to the high sensitivity site specification screen 700 described later.

In the above description, a numerical value of the radius indicating the size of the CT imaging area CA is input to the text box 631. Alternatively, the size of the CT imaging area CA may be adjusted as follows. The CT imaging area line 613 defining a perfect circle centered around the point specified by the specification cursor 612 is displayed as overlapping the dental arch image 611, and a point on the CT imaging area line 613 is held by the specification cursor 612 to adjust the size of the CT imaging area CA.

The X-ray imaging device 1 may be structured such that the mode is switched when the specification cursor 612 is operated to change the shape of the CT imaging area line 613. For example, the X-ray imaging device 1 may be structured such that the perfect circle mode is changed to the ellipse mode when the specification cursor 612 is operated to change the shape of the CT imaging area line 613 from a perfect circle to an ellipse.

In this manner, a perfectly circular CT imaging area CA can be set on, for example, a local imaging target site OB including two or three left molars. Therefore, an X-ray can be directed to only the imaging target site OB, which is an area of interest, in a limited manner, and also the CT imaging area CA can be set on a desired area.

The CT imaging area CA can be set to have any of various shapes instead of a perfect circle. In accordance with the size or range of the imaging target site OB as an area of interest, or the position of the imaging target site OB in the dental arch DA, the CT imaging area CA can be set to have an elliptical, generally triangular, oval or any of various other shapes along the curved shape of the dental arch DA. Owing to this, the imaging target site OB as an area of interest can be imaged with certainty while the unnecessary X-ray exposure dose is decreased. In addition, the imaging target site OB determined based on the diagnosis, the symptom or the like is prevented as much as possible from being unnecessarily exposed to the X-ray, and the applicability of the X-ray imaging device 1 can be improved.

Now, the high sensitivity site specification screen 700 displayed as the high sensitivity site setting section 62b on the operation panel 62 will be described. As shown in FIG. 6, the high sensitivity site specification screen 700 is a screen to set a high sensitivity site H with respect to the CT imaging area CA set on the imaging area setting screen 600. The high sensitivity site specification screen 700 includes an image display section 710 that displays a high sensitivity site H, a property display section 720 that displays detailed information on the high sensitivity site H, and a condition setting section 730.

The image display section 710 displays a high sensitivity site side image 711 that shows the high sensitivity site H on a side view image of the subject M1, a specification cursor (pointer) 712 that specifies the high sensitivity site H displayed as overlapping the high sensitivity site side image 711, and a planar direction cross-sectional view image 713. The planar direction cross-sectional view image 713 shows a cross-sectional view of the subject M1, in a planar direction, encompassing the high sensitivity site H specified by the specification cursor 712.

The high sensitivity site side image 711 and the planar direction cross-sectional view image 713 are each an example of high sensitivity specification image that specifies a high sensitivity specification H. Preferably, the high sensitivity site side image 711 and the planar direction cross-sectional view image 713 are each a schematic illustration or the like of the head of the subject M1. The size and shape of the head is based on the size and shape of a head having a standard bone structure. An internal structure including hard tissue and important soft tissue may be illustrated to some extent.

As the high sensitivity site side image 711 or the planar direction cross-sectional view image 713, a plurality of high sensitivity site specification images may be prepared for various body sizes. Alternatively, a plurality of high sensitivity site specification images may be prepared for adults and children or for men and women.

The high sensitivity site specification image may be an X-ray image acquired by actually imaging the subject M1 or may be a schematic illustration or the like of the head of the subject M1. In the latter case, there is an advantage that the subject M1 is prevented from being exposed to the X-ray.

In FIG. 6, the high sensitivity site side image 711 shows parotid gland Ha and submandibular gland Hb as the high sensitivity sites H. Since the specification cursor 712 specifies the parotid gland Ha, the planar-direction cross-sectional view image 713 shows the parotid gland Ha. The cross-sectional view image 713 shows the CT imaging area CA set on the imaging area setting screen 600 together with right and left parotid gland Har and Hal. When the specification cursor 712 specifies the submandibular gland Hb in the high sensitivity site side image 711, the planar-direction cross-sectional view image 713 shows the submandibular gland Hb. The specification cursor 712 may specify the high sensitivity site H shown in the cross-sectional view image 713.

The high sensitivity site side image 711 may be an image of the head seen from a lateral side, from the front side or at any other angle. The high sensitivity site side image 711 may include images seen at a plurality of angles, for example, images seen from a lateral side and the front side.

Alternatively, one of the high sensitivity sites H shown in the high sensitivity site side image 711 may be retrieved and displayed independently.

As shown in FIG. 6, the high sensitivity site side image 711 may show the dental arch DA or the CT imaging area CA in an overlapping manner.

The X-ray imaging device 1 may be structured such that even without the operator specifying the high sensitivity site H in the high sensitivity site side image 711, all the registered high sensitivity sites H are shown in the planar direction cross-sectional view image 713.

The planar direction cross-sectional view image 713 may show only a high sensitivity site H which is at the same level as the CT imaging area CA. In this case, even when the operator specifies the submandibular gland Hb in the high sensitivity site side image 711, the planar direction cross-sectional view image 713 does not show the submandibular gland Hb unless the submandibular gland Hb is at the same level as the CT imaging area CA.

The property display section 720 displays the detailed information on the high sensitivity site H specified, for example, in the high sensitivity site side image 711 or by the specification cursor 712. In more detail, the property display section 720 includes a name display section 721 that displays a name of the high sensitivity site H specified by the specification cursor 712, a priority level setting and display section 722 to set or display a priority level of the high sensitivity site H, a major axis setting and display section 723 to set or display the length of a major axis among various factors representing the size of the high sensitivity site H as seen in the Z-axis direction, and a minor axis setting and display section 724 to set or display the length of a minor axis of the high sensitivity site H.

The priority level setting and display section 722, the major axis setting and display section 723 and the minor axis setting and display section 724 each have a text box, in which a priority level or length based on preset information is stored and displayed. In order to change such a priority level or length, another priority level of length can be directly input to the text box.

The condition setting section 730 includes a Set button 731, a Reset button 732, a Start button 733, a FreeStart button 734, and a Return button 735.

The Set button 731 is an operation button to save the high sensitivity site H specified by the specification cursor 712 and the detailed information on the high sensitivity site H set and displayed in the property display section 720.

The Reset button 732 is an operation button to reset the specification of the high sensitivity site H specified by the specification cursor 712 and the detailed information set and displayed in the property display section 720.

The Start button 733 is an operation button to instruct start of CT imaging on the CT imaging area CA based on the settings saved by the Set button 731.

The FreeStart button 734 is an operation button to start CT imaging with no consideration of the high sensitivity site H although the high sensitivity site H located in the vicinity of the CT imaging area CA which is specified by the imaging area setting screen 600 is shown in the high sensitivity site side image 711 or the cross-sectional view image 713.

The Return button 735 is an operation button to return the high sensitivity site specification screen 700 to an initial screen (not shown)

The imaging area setting screen 600 may act as the revolving arm trajectory setting section 60b. In this case, the high sensitivity site H is displayed as overlapping the dental arch image 611.

The X-ray imaging device 1 may allow the operator to specify a desired position as a high sensitivity site H. The X-ray imaging device 1 may allow the operator to input a range of the high sensitivity site H. For example, the X-ray imaging device 1 may be structured such that even the high sensitivity site specification screen 700, or the imaging area setting screen 600 acting as the revolving arm trajectory setting section 60b, may allow the operator to set a high sensitivity site H by drawing the high sensitivity site H with a stylus or the like in the image display section 710 or the image display section 610.

Hereinafter, with reference to FIG. 7, a method for performing CT imaging on an imaging target site OB such that the exposure dose of the high sensitivity site H is decreased by use of the X-ray imaging device 1 having the above-described structure will be described in detail.

The dental arch DA includes the teeth on the front side including anterior teeth, teeth on the left molar side including left molar teeth, and teeth on the right molar side including right molar teeth. In the following example, one of the left molar teeth in the dental arch DA is the imaging target site OB.

In the following example, the submandibular gland Hb is the high sensitivity site H, the exposure dose of which is controlled to be decreased.

First, for performing the CT imaging, the subject M1 is fixed with respect to the main body part 2 accommodated in the X-ray-proof chamber 70 by use of the subject holding section 421.

In this state, the imaging area setting screen 600 is displayed on the display section 61 by an operation made by the operator, so that an imaging mode is selectable by use of the Mode button 644 (step s1). When the Mode button 644 displayed on the imaging area setting screen 600 is pressed to select the panorama mode (step s2: Yes), the X-ray imaging device 1 performs panorama imaging on the subject M1 (step s3).

For performing the panorama imaging, the X-ray imaging device 1 controls, by use of the main body control section 60, the X-ray radiation range restriction section driving sections 16 that controls the driving of the beam formation mechanism 13. The control is performed such that the distance between the edges 14c of the upper length direction X-ray radiation restriction section 14a and the lower length direction X-ray radiation restriction section 14b is adjusted to be long, and such that the distance between the edges 15c of the left lateral direction X-ray radiation restriction section 15a and the right lateral direction X-ray radiation restriction section 15b is short. In this way, the opening 17 is put into a rectangular shape longer in the length direction as seen in a front view. Thus, an X-ray slit beam having a conical shape longer in the length direction is directed toward the X-ray detection section 20 and the panorama imaging is performed.

Alternatively, there may be the following case. In the imaging area setting screen 600, the Mode button 644 is not pressed or the Mode button 644 is pressed to select an ellipse mode or a perfect circle mode (step s2: No). In the dental arch image 611 in the image display section 610, the imaging target site OB is set by the specification cursor 612. A numerical value is input to the text box 631 in the selection range setting section 630. The Next button 643 is pressed and the setting on a CT imaging area CA is accepted (step s4). In this case, the X-ray imaging device 1 displays the high sensitivity site specification screen 700 in the display section 61.

When, on the high sensitivity site specification screen 700, the FreeStart button 734 is pressed, or no high sensitivity site H is specified by the specification cursor 712 and the Start button 733 is pressed (step s5: No), it is determined that the exposure dose does not need to be decreased and common CT imaging is performed (step s6).

For forming the CT imaging area CT set on the imaging area setting screen 600 in such common CT imaging, the X-ray imaging device 1 controls, by use of the main body control section 60, the X-ray radiation range restriction section driving sections 16 that controls the driving of the beam formation mechanism 13. The control is performed such that the distance between the length direction X-ray radiation restriction sections 14, and the distance between the lateral direction X-ray radiation restriction sections 15, are short. In this way, the opening 17 is put into a square shape, as seen in a front view, smaller than the shape in the case where common large viewfield CT imaging is performed. Thus, an X-ray cone beam for a small viewfield that has a conical shape is directed toward the X-ray detection section 20. In addition, as shown in FIG. 8 and FIG. 9, the elevation section 41a is controlled to adjust the height of the revolving arm 30 with respect to the imaging target site OB of the subject M1. Thus, the CT imaging on a small viewfield is performed.

This will be described in more detail. Referring to FIG. 8, when the imaging target site OB is in the upper jaw, the main body control section 60 raises the revolving arm 30 in the Z-axis direction from the position of the revolving arm 30 for common large viewfield CT imaging (represented by the dashed line). At this position in the height direction, the revolving arm 30 is revolved to perform the CT imaging on the imaging target site OB in the upper jaw.

By contrast, referring to FIG. 9, when the imaging target site OB is in the lower jaw, the main body control section 60 lowers the revolving arm 30 in the Z-axis direction from the position of the revolving arm 30 for common large viewfield CT imaging (represented by the dashed line) and also from the position of the revolving arm 30 when the imaging target site OB is in the upper jaw. At this position in the height direction, the revolving arm 30 is revolved to perform the CT imaging on the imaging target site OB in the lower jaw.

The common CT imaging performed in step S6 may be performed on a large viewfield instead of a small viewfield described above.

The CT imaging area CA of a large viewfield may cover the entire head, the entire jaw bone or the entire dental arch, in the horizontal direction.

The X-ray imaging device 1 may be structured such that one of CT imaging on a large viewfield and CT imaging on a small viewfield is selectable. Alternatively, the X-ray imaging device 1 may be structured such that one of CT imaging on a large viewfield, CT imaging on a small viewfield, and CT imaging on a single or a plurality of middle viewfields between the small viewfield and the large viewfield is selectable. Still alternatively, the X-ray imaging device 1 may be structured such that any size of viewfield between the small viewfield and the large viewfield can be selected with no stage being set.

The X-ray imaging device 1 may be structured such that any size of viewfield may be set between the small viewfield and the middle viewfield with no stage being set, or such that CT imaging is performed only on a middle viewfield.

In the above example, the main part control section 60 controls the X-ray radiation range restriction section driving sections 16 to drive the beam formation mechanism 13 so that an X-ray cone beam Bx for a small viewfield is formed by the opening 17 having a small square shape as seen in a front view. Alternatively, the main body control section 60 may control the revolution shaft moving section 30m of the revolving arm driving section 30K such that the X-ray generation section 10 including the X-ray generator 10a approaches the subject M1. As a result of this, the X-ray cone beam Bx directed toward the imaging target site OB has a smaller cross-section, and the CT imaging is performed on a small viewfield.

By contrast to the CT imaging in which the exposure dose does not need to be decreased, there may be the following case. In the high sensitivity site specification screen 700, the submandibular gland Hb is specified as the high sensitivity site H by the specification cursor 712 (step s5: Yes), and the detailed information on the high sensitivity site H is input to the property display section 720. Alternatively, the Start button 733 is pressed without the detailed information being input (step s7). In this case, it is determined that the exposure dose of the submandibular gland Hb needs to be decreased. The X-ray imaging device 1 calculates the necessity degree of each of control on the revolution range L of the revolving arm 30 and control on the revolution plane of the revolving arm 30, based on the CT imaging area CA set on the imaging area setting screen 600 and the submandibular gland Hb specified on the high sensitivity site specification screen 700.

This will be described in more detail. The main body control section 60 of the X-ray imaging device 1 makes a calculation to find whether it is sufficient to perform either one of the revolution range control and the revolution plane control or whether both of the controls need to be performed, in order to decrease the exposure dose of the submandibular gland Hb. The revolution range control is to control the revolution start position Ls and a revolution end position Le in the revolution range L of the revolving arm 30. The revolution plane control is to control the revolution plane based on the level in the height direction of the revolving arm 30 and the inclination angle of the revolving arm 30, namely, the radiation angle of the X-ray cone beam, with respect to the subject M1. Such a calculation is performed by use of the revolving arm trajectory setting section 60b and the revolving arm driving control section 60c based on the position or size of the CT imaging area CA and the submandibular gland Hb.

When it is found to be sufficient to perform one of the revolution range control and the revolution plane control (step s8: No), and when it is further found to be sufficient to perform the revolution range control (step s9: Yes), the main body control section 60 calculates and sets the revolution start position Ls and the revolution end position Le of the revolving arm 30 (step s10), and controls the X-ray radiation range restriction section driving sections 16 to adjust the beam formation mechanism 13 in accordance with the CT imaging area CA (step s11). Thus, the CT imaging is performed (step s12).

The X-ray imaging device 1 may be structured such that in the case where the calculation results show that it is not necessary to decrease the exposure dose and that it is sufficient to perform common CT imaging based on the position and range of the CT imaging area CA, the common CT imaging is automatically performed, or it may be so notified.

This will be described in more detail. FIG. 10 shows a trajectory of rotation of the X-ray cone beam Bx when the revolving arm 30 revolves over 180 degrees in the common CT imaging for which the exposure dose of the high sensitivity site H does not need to be decreased. Now, it is assumed as shown in FIG. 10 that the revolution start angle of the revolving arm 30 at the revolution start position Ls of the revolution range L and the revolution end angle of the revolving arm 30 at the revolution end position Le are always set to be the same angle regardless of the relationship between the position of the CT imaging area CA and the position of the high sensitivity site H.

In the example of FIG. 10, the revolution range L of the revolving arm 30 shows the revolution range on the X-ray generation section 10 side.

In this state, as shown in FIG. 10, the left submandibular gland Hbl is close to the CT imaging area CA which is set on a left part of the dental arch DA. Therefore, the left submandibular gland Hbl is irradiated with the X-ray cone beam Bx over 180 degrees in which the revolving arm 30 revolves. The right submandibular gland Hbr, which is farther from the CT imaging area CA than the left submandibular gland Hbl, is passed by the X-ray cone beam Bx in a first half and a second half of the revolution of the revolving arm 30, and is partially irradiated double.

FIG. 11 shows a trajectory of rotation of the X-ray cone beam Bx when the revolution start position Ls of the revolution range L is set to a position rightward and forward with respect to the revolution start position Ls shown in FIG. 10. The revolution end position Le is set to a position which is away from the revolution start position Ls by 180 degrees. Such settings are provided in order to decrease the exposure dose of the submandibular gland Hb.

In the example shown in FIG. 10 and FIG. 11, the revolving arm 30 revolves over 180 degrees to perform the CT imaging. In order to acquire a CT image having a better quality, it is preferable to acquire projection data of at least 180 degrees on any position in the CT imaging area CA.

In order to realize this, CT imaging may be performed as follows. The X-ray cone beam Bx is directed to acquire projection data while the revolving arm 30 is revolved over an angle which is a sum of 180 degrees and an expansion angle of the X-ray cone beam Bx as seen in the Z-axis direction, namely, over an angle which is a sum of 180 degrees and a fan angle. As the revolution range L of the revolving arm 30 is larger, the probability that the X-ray cone beam Bx is directed to the high sensitivity site H is higher. However, the X-ray exposure dose can be decreased by the above-described structure.

This will be described specifically. As shown in FIG. 11, the revolution start position Ls of the revolution range L is set to a position rightward and forward with respect to the revolution start position Ls shown in FIG. 10, based on the CT imaging area CA and the submandibular gland Hb. In this case, the left submandibular gland Hbl is close to the CT imaging area CA like in the case where the common CT imaging is to be performed with no control on the exposure dose. However, the right submandibular gland Hbr, which is away from the CT imaging area CA, is prevented from being irradiated double with the X-ray cone beam Bx. Therefore, the exposure dose of the right submandibular gland Hbr can be decreased.

This will be described in more detail. Referring to FIG. 12, when CT imaging is to be performed with the X-ray cone beam Bx directed from the X-ray generator 10a of the X-ray generation section 10 toward the X-ray detection section 20, more specifically, the X-ray detector 20a, the X-ray cone beam Bx revolves about the imaging target site OB in the CT imaging area CA. When seen in an axial direction of the revolution shaft 31, the X-ray cone beam Bx can be divided into an area g between the X-ray generator 10a and the CT imaging area CA and an area d between the X-ray detection section 20 and the CT imaging area CA.

Referring to FIG. 13, when the X-ray cone beam Bx is revolved over 180 degrees to perform CT imaging, an area G is formed by the trajectory of the area g whereas an area D is formed by the trajectory of the area d. The area GD in which the area G and area D overlap each other is formed.

When the submandibular glands Hb (Hbl, Hbr) are specified as the high sensitivity sites H, the trajectory of the X-ray generator 10a of the X-ray generation section 10 and the trajectory of the X-ray detection section 20 (namely, the trajectory of the revolving arm 30) are set such that the area GD is offset from the submandibular glands Hb (Hbl, Hbr).

As can be seen, the revolution range control of controlling the trajectory of the revolving arm 30, namely, the revolution range L of the revolving arm 30 merely needs to be performed such that the area GD is offset from the submandibular glands Hb (Hbl, Hbr). Thus, the revolution range control has a certain degree of freedom. In consideration of the imaging efficiency, the revolution range control may be performed as follows.

The subject M1 is guided into the X-ray-proof chamber 70 in the state where the revolving arm 30 is at a wait position thereof, which is usually set commonly to all the modes. A position which has the shortest distance from the wait position, in such an area that the area GD is offset from the submandibular glands Hb (Hbl, Hbr), is set as the revolution start position Ls. The standby switch 65a is operated to move the revolving arm 30 from the wait position to the revolution start position Ls. Then, the imaging actuation switch 65b is operated to revolve the revolving arm 30 over 180 degrees. Thus, the CT imaging is performed.

The revolution range L of the revolving arm 30 is set in this manner, so that the wait time of the subject M1 for the CT imaging can be shortened.

Referring to FIG. 8, when the X-ray imaging device 1 has a mechanical structure in which the subject M1 is to face the support pillar 50, the subject M1 is often guided to move toward the support pillar 50 when entering the X-ray-proof chamber 70.

When exiting the X-ray-proof chamber 70, the subject M1 is often guided to move away from the support pillar 50.

Therefore, the common wait position of the revolving arm 30 is often set to the revolution start position Ls as shown in FIG. 10, or the orientation of the ran 30 is slightly inclined from the inclination when the revolving arm 30 is at the revolution start position Ls. In either case, neither the X-ray generation section 10 nor the X-ray detection section 20 obstructs entrance of the subject M1.

Oppositely, the revolution end position L3 of the revolving arm 30 is often set such that neither the X-ray generation section 10 nor the X-ray detection section 20 obstructs exit of the subject M1.

Preferably in the X-ray imaging device 1, the wait position of the revolving arm 30 when the subject M1 enters the X-ray-proof chamber 70 and the revolution end position Le when the subject M1 exits the X-ray-proof chamber 70 are set such that at least one of the entrance and the exit of the subject M1 is made with no obstruction by the X-ray generation section 10 or the X-ray detection section 20.

When no high sensitivity site H is specified, the CT imaging may be performed from the common wait position.

As described above, the X-ray imaging device 1 is structured such that the wait time of the subject M1 for the CT imaging can be shortened. Therefore, the CT imaging can be performed with the entrance or the exit of the subject M1 being not much obstructed and with a short wait time.

The control of setting the revolution range L may be performed manually by the operator. Alternatively, candidate areas in accordance with the specified submandibular glands Hb may be stored on the storage section 64.

The trajectory of the revolving arm 30, namely, the revolution range L of the revolving arm 30 may be calculated each time based on the specified high sensitivity site H. Alternatively, a table may be stored on the storage section 64, so that the revolution range L can be found automatically.

In the structure of the X-ray imaging device 1, the subject M1, namely, the test subject, is positioned to face the support pillar 50. There is no specific limitation on the positional relationship between the orientation of the subject M1 and the support pillar 50.

For example, the X-ray imaging device 1 may be structured such that the support pillar 50 is located to the side of, namely, to the left of, or to the right of, the subject M1.

In this example, as shown in FIG. 8, the X-ray imaging device 1 is structured such that the subject M1 faces the support pillar 50. Alternatively, for example, the X-ray imaging device 1 may be structured such that the support pillar 50 is located to the left of the subject M1 when seen in a front view, namely, is located to the right of the subject M1 when seen in a rear view.

Still alternatively, the support pillar 50 and the elevation section 41a may be omitted. In this case, for example, an arm-like support member having one end fixed to the wall and extending horizontally from the wall may be used. The revolution shaft 31 of the revolving arm 30 may be axially supported by the other end of the arm-like support member.

In any structure, it is preferable that the wait position of the revolving arm 30 and the revolution end position Le are set such that at least one of the entrance and the exit of the subject M1 is made with no obstruction by the X-ray generation section 10 or the X-ray detection section 20.

As described above, the X-ray imaging device 1 is structured such that the wait time of the subject M1 for the CT imaging can be shortened. Therefore, the CT imaging can be performed with the entrance or the exit of the subject M1 being not much obstructed and with a short wait time.

In the CT imaging in which the exposure dose of the submandibular gland Hb dose needs to be decreased, there may be the following case. A calculation is made to find whether it is sufficient to perform either one of the revolution range control and the revolution plane control is necessary or whether both of the controls need to be performed, based on the CT imaging area CA set on the imaging area setting screen 600 and the submandibular gland Hb specified on the high sensitivity site specification screen 700. When it is found to be sufficient to perform one of the revolution range control and the revolution plane control (step s8: No), and when it is further found to be sufficient to perform the revolution range control (step s9: NO), the main body control section 60 controls the revolution shaft moving section 30*m* and the elevation section 41*a* of the revolving arm driving section 30K to adjust the height and/or angle of the revolving arm 30 with respect to the subject M1 (step s13). In addition, the main body control section 60 controls the X-ray detection section driving section 23 and the X-ray radiation range restriction section driving sections 16 to adjust the heights of the X-ray generation section 10 and the X-ray detection section 20 (step s14), and controls the beam formation mechanism 13 to partially block the X-ray and thus to adjust the radiation direction of the X-ray cone beam Bx (step s15). Thus, the CT imaging is performed (step s16).

The method of the above-described control in the case where CT imaging is to be performed on the CT imaging area CA in the upper jaw will be described. If the revolving arm 30 is revolved at the height and radiation angle as shown in FIG. 8, the expose dose of the parotid gland Ha is increased. Referring to FIG. 14, in order to decrease the expose dose of the parotid gland Ha, the revolving arm 30 is moved downward and the beam formation mechanism 13 is adjusted such that the X-ray cone beam Bx is directed slightly upward.

The X-ray detector 20*a* is moved upward or downward by the X-ray detection section driving section 23 such that the X-ray detector 20*a* can receive the X-ray cone beam Bx even when the X-ray cone beam Bx is directed upward or downward. In the state shown in FIG. 14, the X-ray cone beam Bx is directed slightly upward, and thus the X-ray detector 20*a* is moved upward.

Alternatively, the X-ray detector 20*a* may have a large detection surface in the up-down direction so that the X-ray detector 20*a* can receive the X-ray cone beam Bx even when the X-ray cone beam Bx is directed upward or downward. In this case, the X-ray detection section driving section 23 may be omitted.

The method of the above-described control in the case where CT imaging is to be performed on the CT imaging area CA in the lower jaw will be described. If the revolving arm 30 is revolved at the height and radiation angle as shown in FIG. 9, the expose dose of the thyroid gland Hc (FIG. 15) is increased. Referring to FIG. 15, in order to decrease the expose dose of the thyroid gland Hc, the revolving arm 30 is moved upward and the beam formation mechanism 13 is adjusted such that the X-ray cone beam Bx is directed slightly downward.

As long as the X-ray cone beam Bx is offset from the thyroid gland Hc, it is not necessary to change the height of the revolving arm 30, the height of the X-ray detector 20*a* or the radiation direction of the X-ray cone beam Bx during the CT imaging. When, for example, it is wished that the X-ray cone beam Bx is not directed toward the other high sensitivity sites H, the radiation direction of the X-ray cone beam Bx may be moved upward or downward by the beam formation mechanism 13, and the height of the X-ray detector 20*a* may be changed by the X-ray detection section driving section 23 in accordance with the position at which the X-ray cone beam Bx is received, during the CT imaging.

As described above, the revolution plane control adjusts the height of the revolving arm 30 with respect to the subject M1 and also adjusts the radiation direction of the X-ray cone beam Bx, namely, the inclination of revolution plane. Referring to FIG. 16, when the X-ray cone beam Bx is directed from the front side of the head of the subject M1, the radiation direction of the X-ray cone beam Bx, namely, the revolution plane, is inclined upward in order to decrease the exposure dose.

The X-ray imaging device 1 is also usable for otorhinology. Referring to FIG. 17, it is now assumed that an area of the auditory ossicles or the vicinity thereof is the CT imaging area CA and the X-ray cone beam Bx is directed from the rear side of the head of the subject M1. If the X-ray cone beam Bx is directed horizontally, the lens Im of the eyeball I is on the radiation path of the X-ray cone beam Bx. In order to decrease the exposure dose of the lens Im, the radiation direction of the X-ray cone beam Bx, namely, the revolution plane, is inclined downward.

In order to avoid distortion of images, it is preferable that the X-ray cone beam Bx from the X-ray generation section 10 is perpendicularly incident on the X-ray detection 20. Therefore, the heights of the X-ray generation section 10 and the X-ray detection section 20 are set such that the X-ray cone beam Bx is inclined at a minimum possible angle at which the X-ray cone beam Bx is offset from the high sensitivity site H.

In the case described above, it is sufficient to perform either one of the revolution range control and the revolution plane control is necessary. By contrast, there is a case where it is found that both of the revolution range control and the revolution plane control are necessary (step s8: Yes). In this case, the main body control section 60 calculates and sets the revolution start position Ls and the revolution end position Le (step s17). In addition, the main body control section 60 controls the revolution shaft moving section 30*m* and the elevation section 41*a* of the revolving arm driving section 30K to adjust the height and/or angle of the revolving arm 30 with respect to the subject M1 (step s18). The main body control section 60 further controls the X-ray detection section driving section 23 and the X-ray radiation range restriction section driving sections 16 to adjust the heights of the X-ray generation section 10 and the X-ray detection section 20 (step s19), and controls the beam formation mechanism 13 to partially block the X-ray and thus to adjust the radiation direction of the X-ray cone beam Bx (step s20). Thus, the CT imaging is performed (step s21).

The X-ray imaging device 1 performs at least one of the revolution range control and the revolution plane control based on the CT imaging area CA set on the imaging area setting screen 600 and the high sensitivity site H set on the high sensitivity site specification screen 700, so that CT imaging is performed on the CT imaging area CA with certainly while the exposure dose of the high sensitivity site H is decreased.

In the above example, one high sensitivity site H displayed on the high sensitivity site specification screen 700 in an overlapping manner is specified for one CT imaging area CA, and the exposure dose thereof is decreased. Hereinafter, a method for decreasing the exposure dose of a plurality of high sensitivity sites H specified for one CT imaging area CA will be described.

In the CT imaging in which the exposure dose of the submandibular gland Hb needs to be decreased, there may be the following case. A calculation is made to find whether it is sufficient to perform either one of the revolution range control and the revolution plane control is necessary or whether both of the controls need to be performed, based on the CT imaging area CA set on the imaging area setting screen 600 and the submandibular gland Hb specified on the high sensitivity site specification screen 700. When it is found to be sufficient to perform one of the revolution range control and the revolution plane control (step s8: No), and when it is further found to be sufficient to perform the revolution range control (step s9: Yes), the process shown in FIG. 18 is performed. When one high sensitivity site H is specified (step t1: No), the main body control section 60 calculates and sets the revolution start position Ls and the revolution end position Le of the revolving arm 30 (step t2) like in step s10. The steps after this are the same as steps s11 and s12 and will not be described.

Now, it is assumed that a plurality of high sensitivity sites H (Ha, Hb) are specified (step t1: Yes) and further that all the high sensitivity sites H (Ha, Hb) can be offset from the revolution trajectory of the X-ray cone beam Bx, namely, the area GD mentioned above (step t3: Yes). In this case, the main body control section 60 calculates and sets the revolution start position Ls and the revolution end position Le such that all the high sensitivity sites H (Ha, Hb) are offset from the area GD (step t4). The steps after this are the same as steps s11 and s12 and will not be described.

Figure 19:
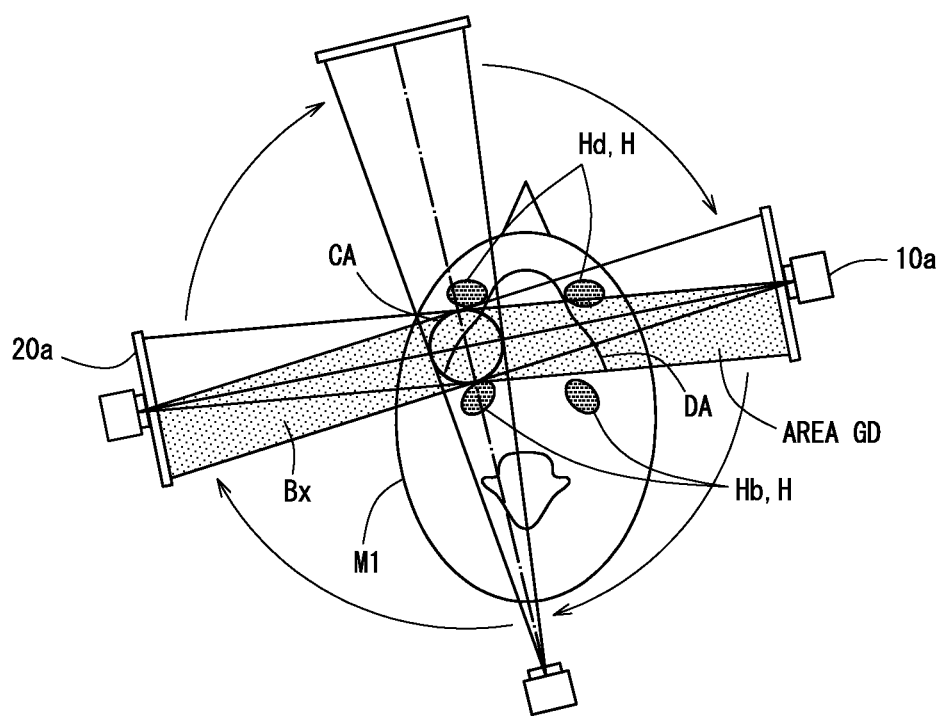
FIG. 19 is a schematic plan view showing exposure dose-suppressed CT imaging performed with the revolution range of the X-ray cone beam being controlled in the case where there are a plurality of high sensitivity sites.

By contrast, when the plurality of high sensitivity sites H (Hd, Hb) cannot be all offset from the area GD (step t3: No), the main body control section 60 calculates and sets the revolution start position Ls and the revolution end position Le such that at least one of the high sensitivity sites H (Hd, Hb) that has a high priority level is offset from the area GD (step t5) as shown in FIG. 19. In the example shown in FIG. 19, high sensitivity sites Hb have a higher priority level than that of high sensitivity sites Hd. The steps after this are the same as steps s11 and s12 and will not be described.

Figure 20:
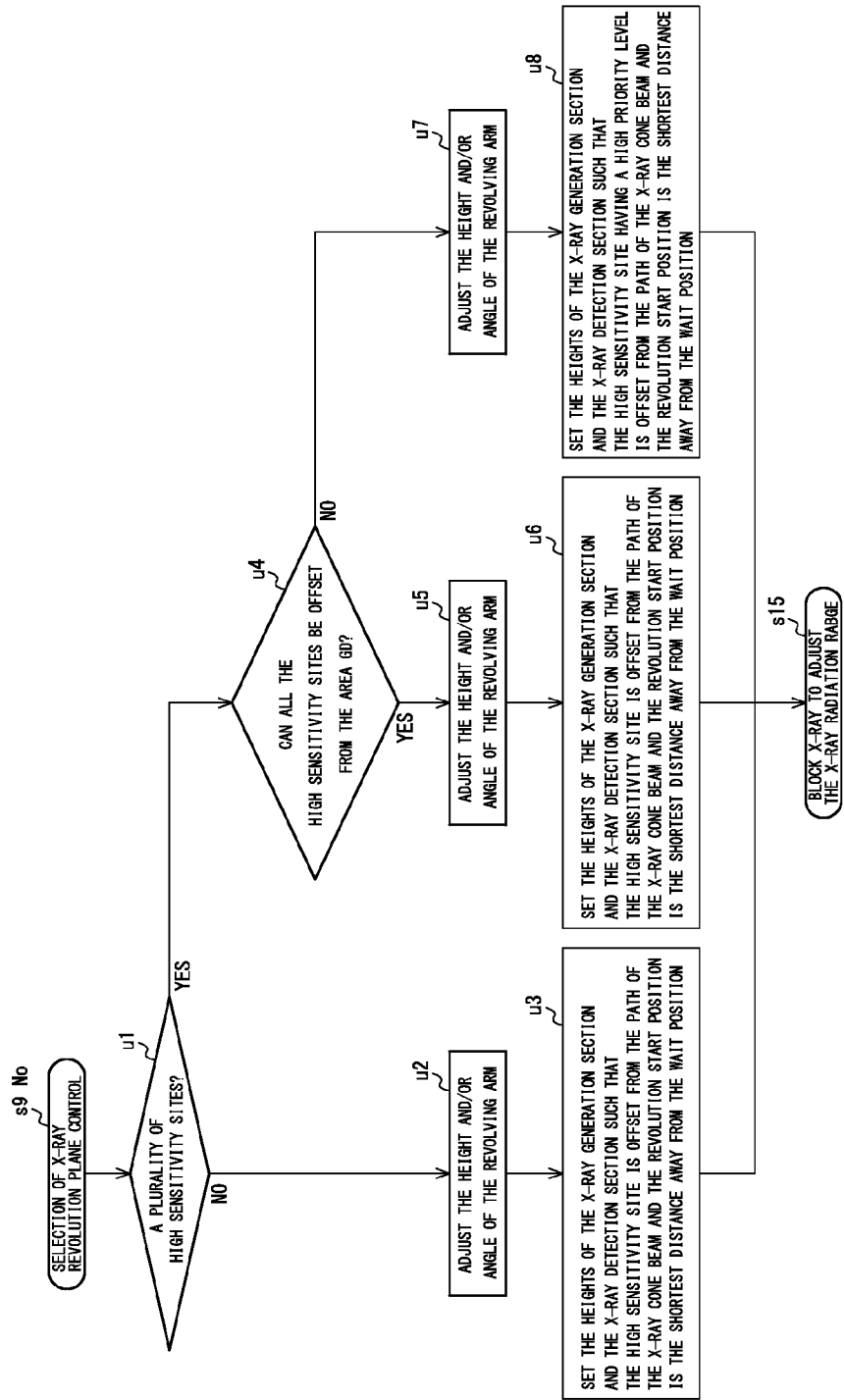
FIG. 20 is a flowchart showing exposure dose-suppressed CT imaging performed with the height and the radiation angle of the X-ray cone beam being controlled in the case where there are a plurality of high sensitivity sites.

When it is found to be sufficient to perform one of the revolution range control and the revolution plane control (step s8: No), and when it is further found to be sufficient to perform the revolution plane control (step s9: No), the process shown in FIG. 20 is performed. When one high sensitivity site H is specified (step u1: No), the main body control section 60 adjusts the height and/or angle of the revolving arm 30 like in step s13 (step u2), and also adjusts the heights of the X-ray generation section 10 ands the X-ray detection 20 such that the specified high sensitivity site H is offset from the revolution trajectory of the X-ray cone beam Bx (step u3). The steps after this are the same as steps s15 and s16 and will not be described.

Figure 21:
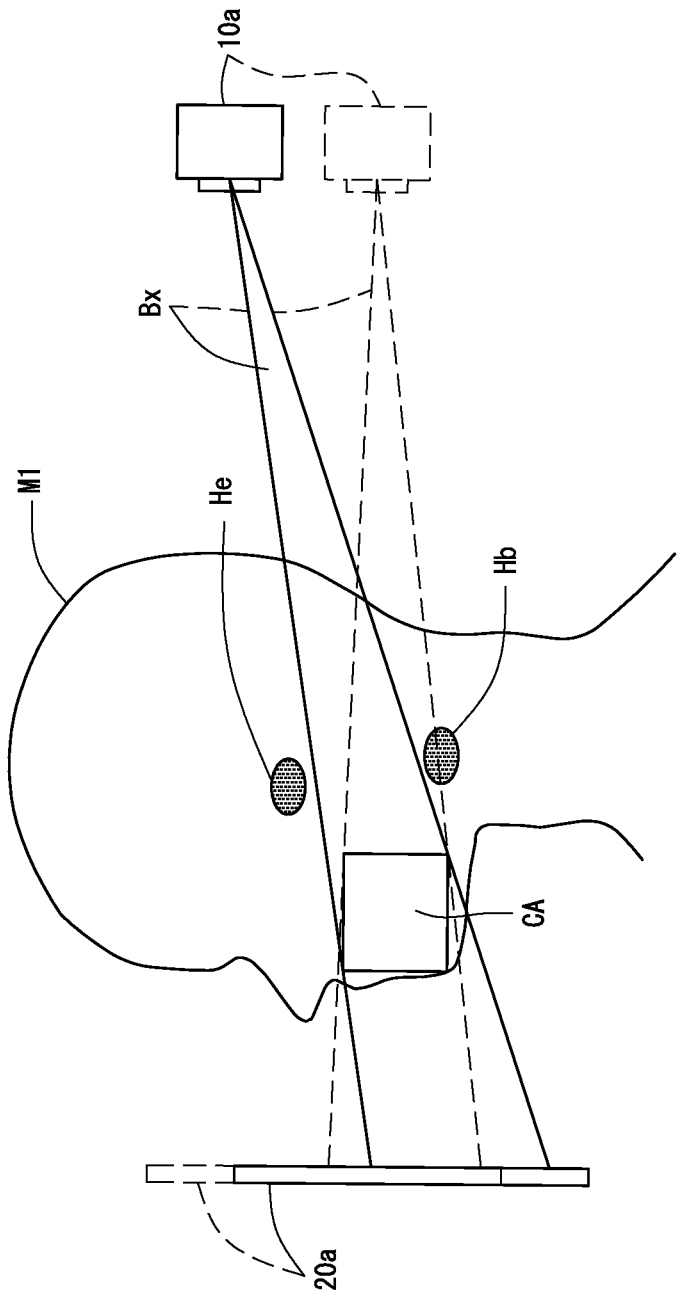
FIG. 21 is a schematic side view showing exposure dose-suppressed CT imaging performed with the height and the radiation angle of the X-ray cone beam being controlled in the case where there are a plurality of high sensitivity sites.
Figure 22:
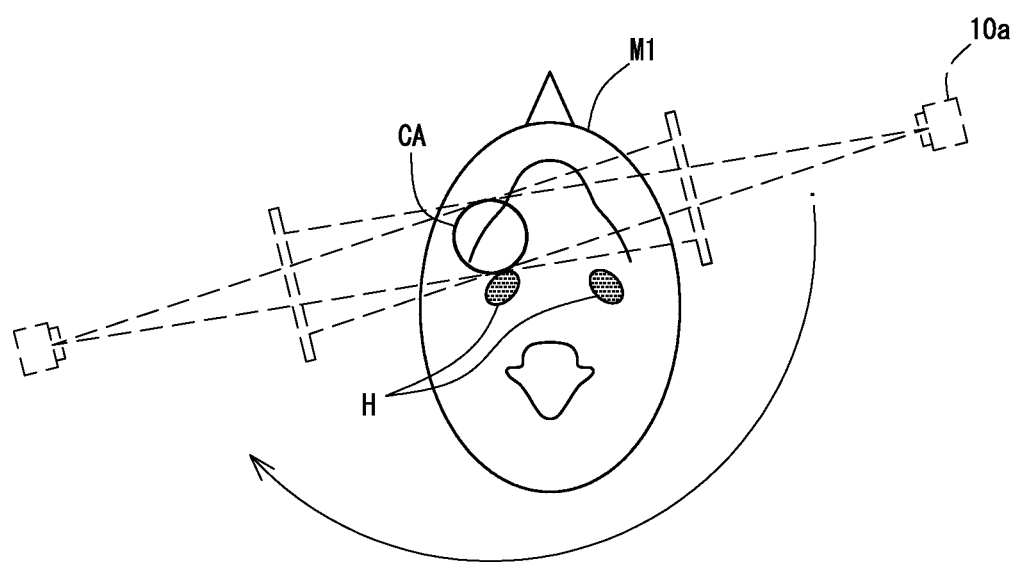
FIG. 22 shows exposure dose-suppressed CT imaging performed with the height and the radiation angle of the X-ray cone beam being controlled in the case where there are a plurality of high sensitivity sites.

Now, it is assumed that a plurality of high sensitivity sites H (Hb, He) are specified (step u1: Yes) and further that all the high sensitivity sites H (Hb, He) can be offset from the revolution trajectory of the X-ray cone beam Bx, namely, the area GD mentioned above (step u4: Yes) as shown in FIG. 21 and FIG. 22. In this case, the main body control section 60 adjusts the height and/or angle of the revolving arm 30 such that all the high sensitivity sites H (Hb, He) are offset from the area GD (step u5), and also adjusts the heights of the X-ray generation section 10 ands the X-ray detection 20 such that all the high sensitivity sites H are offset from the revolution trajectory of the X-ray cone beam Bx (step u6). The steps after this are the same as steps s15 and s16 and will not be described.

By contrast, when the plurality of high sensitivity sites H (Hb, Hf, not shown) cannot be all offset from the area GD (step u4: No), the main body control section 60 adjusts the height and/or angle of the revolving arm 30 such that at least one of the high sensitivity sites H (Hb, Hf) that has a high priority level is offset from the area GD (step u7), and also adjusts the heights of the X-ray generation section 10 ands the X-ray detection 20 such that the at least one high sensitivity site H is offset from the revolution trajectory of the X-ray cone beam Bx (step u8). The steps after this are the same as steps s15 and s16 and will not be described.

As described above, the X-ray imaging device 1 includes the revolving arm 30 that revolves, about the revolution shaft 31, the X-ray generator 10a and the X-ray detector 20a located to face each other while having the subject M1, the revolution driving section 30s that revolves the revolving arm 30 with respect to the subject M1, the imaging area setting screen 600 that accepts the setting of a local area of the subject M1 as the CT imaging area CA, and the main body control section 60 that controls at least the revolution driving section 30s. The X-ray imaging device 1 revolves the revolving arm 30 so as to direct the X-ray cone beam Bx toward the CT imaging area CA to perform CT imaging. The X-ray imaging device 1 further includes the high sensitivity site specification screen 700 to specify a high sensitivity site H of a biological body that is sensitive to X-rays from the area GD that revolves during the CT imaging. The main body control section 60 controls at least one of the X-ray revolution plane formed by the X-ray cone beam Bx along with the revolution of the revolving arm 30 and the revolution range L of the revolving arm 30 such that the X-ray exposure dose of the high sensitivity site H specified on the high sensitivity site specification screen 700 is decreased when the X-ray cone beam Bx is directed toward the CT imaging area CA set on the imaging area setting screen 600. (In this specification, the X-ray revolution plane formed by the X-ray cone beam Bx will also be expressed as the "X-ray revolution plane of the revolving arm 30".) Owing to such a structure of the X-ray imaging device 1, even when the high sensitivity site H is in the vicinity of the CT imaging area CA which is set to encompass the imaging target site OB, the imaging target site OB can be imaged with certainty while the exposure dose of the high sensitivity site H is decreased. The "local area" mentioned above is a part of the subject M1 and is displayed as seen in the Z-axis direction.

This will be described in more detail. The main body control section 60 controls at least one of the X-ray revolution plane formed by the X-ray cone beam Bx along with the revolution of the revolving arm 30 and the revolution range L of the revolving arm 30 such that the X-ray exposure dose of the high sensitivity site H specified on the high sensitivity site specification screen 700 is decreased when the X-ray cone beam Bx is directed toward the CT imaging area CA set on the imaging area setting screen 600. Owing to such a structure of the X-ray imaging device 1, even when the high sensitivity site H is in the vicinity of the CT imaging area CA, the imaging target site OB in the CT imaging area CA can be imaged with certainty while the exposure dose of the high sensitivity site H is decreased.

According to the control on the revolution range L performed by the main body control section 60, at least one of the revolution start position Ls and the revolution end position Le in the revolution range L is changed in accordance with the CT imaging area CA set on the imaging area setting screen 600 or the high sensitivity site H specified on the high sensitivity site specification screen 700. Owing to this, the revolution range L of the revolving arm 30 can be adjusted without changing the X-ray revolution plane of the revolving arm 30. Therefore, the exposure dose of the high sensitivity site H specified on the high sensitivity site specification screen 700 can be easily decreased.

According to the control on the revolution plane performed by the main body control section 60, at least one of the X-ray radiation angle with respect to a determined reference plane and the position in the subject M1 to be irradiated with the X-ray is changed in accordance with the CT imaging area CA set on the imaging area setting screen 600 or the high sensitivity site H specified on the high sensitivity site specification screen 700. Owing to this, the imaging target site OB in the CT imaging area CA can be imaged with certainty while the exposure dose of the high sensitivity site H in the vicinity of the imaging target site OB is decreased. The "reference plane" may be, for example, a plane expanding in the horizontal direction at a specific height.

The X-ray imaging device 1 includes the top frame 41 that supports the revolving arm 30 via the revolution shaft 31. The upper frame 41 includes the revolution shaft moving section 30*m* that moves the revolution shaft 31 with respect to the top frame 41, and the elevation section 41*a* that moves the top frame 41 with respect to the subject M1. The main body control section 60 controls the movement of the revolution shaft moving section 30*m* and the elevation section 41*a* to control the X-ray revolution plane. Owing to such a structure, the top frame 41 that supports the revolving arm 30 via the revolution shaft 31 can be moved by the elevation section 41*a*, so that the exposure dose of the high sensitivity H specified on the high sensitivity site specification screen 700 can be easily decreased.

The beam formation mechanism 13 that restricts the X-ray radiation range is provided forward to the X-ray generator 10*a* in the X-ray radiation direction. The main body control section 60 controls the restriction operation of the beam formation mechanism 13 to control the X-ray revolution plane. Owing to this, the X-ray radiation range restricted by the beam formation mechanism 13 can be changed, so that the exposure dose of the high sensitivity H specified on the high sensitivity site specification screen 700 can be easily decreased.

The X-ray imaging device 1 includes the storage section 64 that stores information on the high sensitivity site H. Owing to this, information on the high sensitivity site H such as, for example, the position, size, sensitivity degree, priority level (weighting degree) or the like stored on the storage section 64 can be retrieved. Thus, the CT imaging is performed in such a manner that the exposure dose of the high sensitivity H is decreased.

The CT imaging area CA can be set on the dental arch image 611 displayed on the imaging area setting screen 600, and the high sensitivity site H can be displayed as overlapping the image dental arch image 611. Owing to this, the high sensitivity site H displayed as overlapping the image dental arch image 611 can be visually checked. Therefore, the high sensitivity site H, the exposure dose of which is to be decreased during the CT imaging, can be specified with more certainty.

The X-ray imaging device 1 includes the property display section 720 that changes the high sensitivity site H to be displayed in the image display section 710. Owing to this, the CT imaging can be performed in an appropriate manner in accordance with the situation of the subject M1. For example, a higher priority level is assigned to a high sensitivity site H which is far from the CT imaging area CA but has abnormality occurring, instead of a high sensitivity site H closest to the CT imaging area CA.

The X-ray imaging device 1 includes the standby switch 65*a* and the imaging actuation switch 65*b*. The standby switch 65*a* revolves the revolving arm 30 to the revolution start position Ls in the revolution range L, which is different for each imaging target site OB set on the imaging area setting screen 600. The imaging actuation switch 65*b* revolves the revolving arm 30 while directing the X-ray toward a set area (CT imaging area CA) to perform CT imaging. Owing to this, for example, the standby switch 65*a* is operated to revolve the revolving arm 30 to the revolution start position Ls of the radiation range L to prepare for imaging, and the imaging actuation switch 65*b* is operated to further revolve the revolving arm 30 for CT imaging. Thus, CT imaging can be performed in such a manner that the exposure dose of the high sensitivity site H is decreased.

The X-ray imaging device 1 includes the revolving arm driving section 30K that moves the revolving arm 30. The main body control section 60 drives the revolving arm driving section 30K to move the revolving arm 30. The control to revolve the revolving arm 30 by the main body control section 60 and the control to move the revolving arm 30 by the revolving arm driving section 30K are performed at the same time, so that panorama X-ray imaging can be performed. Owing to this, when a panorama image is needed, panorama X-ray imaging can be performed with no need to prepare another X-ray imaging device.

The X-ray imaging device may include the cephalostat 43 located perpendicularly to the revolution shaft 31. In this case, when a cephalogram is needed, cephalo X-ray imaging can be performed with no need to prepare another X-ray imaging device.

The X-ray generation source according to one or more embodiments of the present invention corresponds to the X-ray generator 10*a* in the above-described embodiment;

the electric X-ray detector corresponds to the X-ray detection section 20;

the revolution section corresponds to the revolving arm 30;

the X-ray radiation area corresponds to the CT imaging area CA;

the X-ray radiation area setting section corresponds to the imaging area setting screen 600;

the control section corresponds to the main body control section 60;

the X-ray CT imaging device corresponds to the X-ray imaging device 1;

the X-ray flux corresponds to the X-ray cone beam Bx;

the area where the X-ray flux passes corresponds to the area GD;

the high sensitivity site corresponds to the high sensitivity site H, the parotid gland Ha, the left parotid gland Hal, the right parotid gland Har, the submandibular gland Hb, the left submandibular gland Hbl, the right submandibular gland Hbr, the thyroid gland Hc, and the lens Im;

the high sensitivity site specification section corresponds to the high sensitivity site specification screen 700;

the X-ray radiation start position corresponds to the revolution start position Ls;

the X-ray radiation end position corresponds to the revolution end position Le;

the support section corresponds to the top frame 41;

the support section moving section corresponds to the elevation section 41*a*;

the shaft moving mechanism corresponds to the revolution shaft moving section 30*m*;

the relative moving mechanism corresponds to the elevation section 41*a*;

the X-ray radiation range restriction section corresponds to the beam formation mechanism 13;

the control pattern storage section and the high sensitivity site information storage section correspond to the storage section 64;

the image containing the X-ray radiation area corresponds to the dental arch image 611;

the high sensitivity site replacing section corresponds to the property display section 720;

the X-ray imaging preparation switch corresponds to the standby switch 65*a*;

the X-ray radiation switch corresponds to the imaging actuation switch 65*b*;

the movement driving section corresponds to the revolving arm driving section 30K; and the cephalo-imaging head fixation device corresponds to the cephalostat 43.

However, the present invention is not limited to the above-described embodiment and may be carried out in any of various other embodiments.

Figure 23:
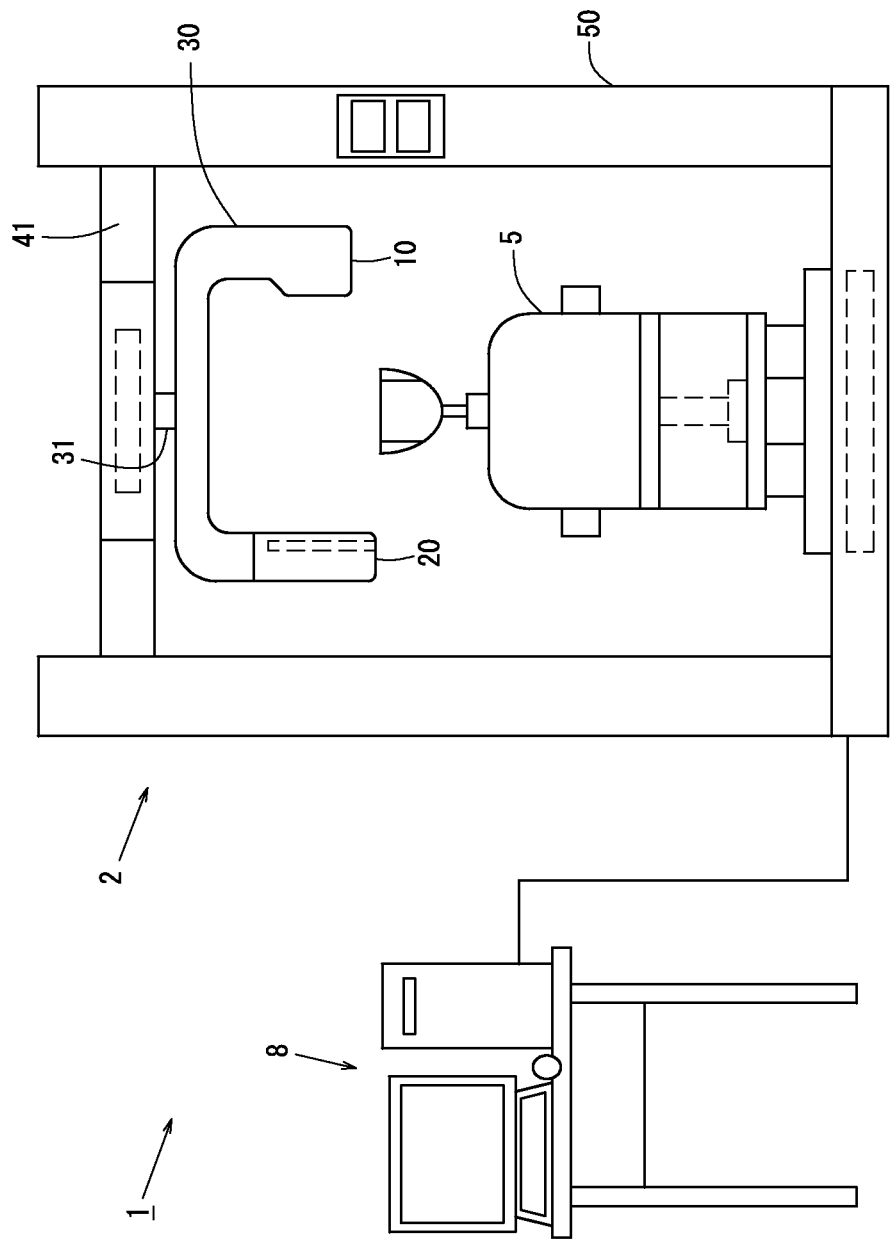
FIG. 23 is a schematic view of another type of X-ray imaging device.
Figure 24:
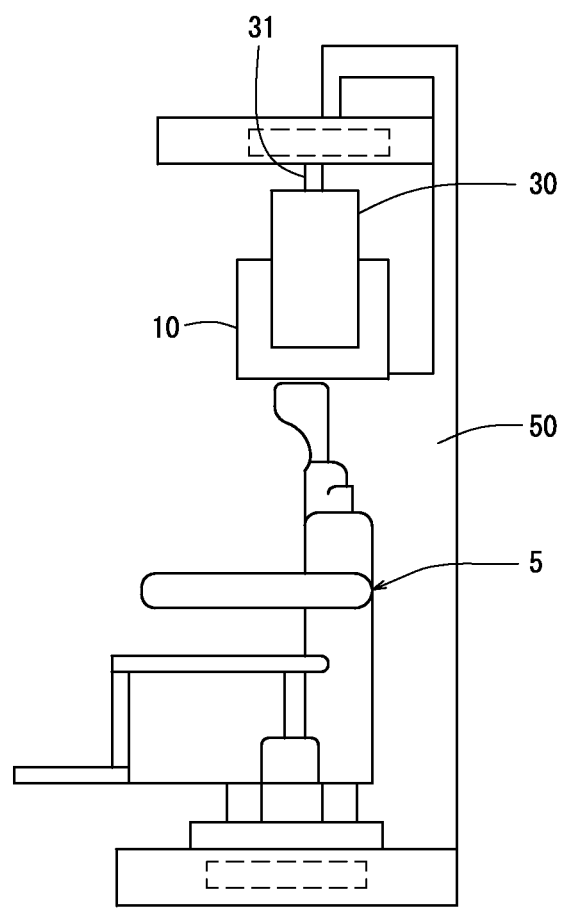
FIG. 24 is a schematic side view of the X-ray imaging device shown in FIG. 23.

For example, in the above-described embodiment, the height of the revolving arm 30 with respect to the subject M1 is adjusted to control the revolution plane of the revolving arm 30. Alternatively, the structure shown in FIG. 23 and FIG. 24 is usable. The revolving arm 30 is supported by the top frame 41 and is not movable in the Z-axis direction. The revolving arm 30 is movable only in the X-axis direction and the Y-axis direction and is revolvable. The height of a chair 5 on which the subject M1 sits is controlled with respect to the revolving arm 30 so that the height of the revolution plane of the revolving arm 30 with respect to the subject M1 is adjusted.

In the above-described embodiment, the revolution range L extends over about 180 degrees. Alternatively, in the case where the exposure dose of the high sensitivity site H is to be decreased by controlling the revolution plane, the revolution range L may extend over about 360 degrees. Still alternatively, DVT imaging or tomosynthesis imaging with no limitation on the revolution range L may be performed.

In the above-described embodiment, the revolving arm 30 is revolved in the horizontal direction. Alternatively, the revolving arm 30 may be inclined while being revolved.

In the above-described embodiment, the high sensitivity site H displayed on the high sensitivity site specification screen 700 in an overlapping manner is specified by the specification cursor 712 in accordance with the CT imaging area CA set on the imaging area setting screen 600. Alternatively, a plurality of high sensitivity sites H may be registered on the storage section 64 so that a high sensitivity site H corresponding to the CT imaging area CA can be automatically specified.

As described above, the control patterns performed by the main body control section 60 may be stored on the storage section 64 as being associated with each CT imaging area CA set on the imaging area setting screen 600. Owing to this, the CT imaging can be performed in such a manner that the exposure dose of the high sensitivity site H is decreased by merely setting the CT imaging area CA by use of the imaging area setting screen 600.

It is not absolutely necessary to display a high sensitivity site H on the high sensitivity site specification screen 700 in an overlapping manner. Alternatively, a high sensitivity site H may be drawn on the high sensitivity site specification screen 700 with the specification cursor 712 or the stylus.

The dental arch image 611 and the image displayed in the image display section 710 may be a scout image, a panorama image, a cephalo image, a schematic illustration or an optically captured photo of the subject M1, or a combination thereof, although this partially overlaps the above description.

Among the detailed information on the high sensitivity site H specified on the a high sensitivity site specification screen 700, the size or position thereof does not need to be input to the property display section 720, but may be set to be changeable by an operation such as drag or the like by use of the specification cursor 712 or the stylus.

The display section 61 may display an X-ray dose such as an irradiation dose, an exposure dose of the patient or the like which is expected when CT imaging is performed.

The radiation dose of the X-ray cone beam Bx may be adjusted based on the position of the X-ray cone beam Bx in the revolution range L during the CT imaging in accordance with the specified high sensitivity site H.

DESCRIPTION OF THE REFERENCE NUMERALS

1 . . . X-ray imaging device
10a . . . X-ray generator
13 . . . Beam formation mechanism
20 . . . X-ray detection section
30 . . . Revolving arm
30K . . . Revolving arm driving section
30m . . . Revolution shaft moving section
30s . . . Revolving driving section
31 . . . Revolution shaft
41 . . . Top frame
41a . . . Elevation section
43 . . . Cephalostat
60 . . . Main body control section
64 . . . Storage section
65a . . . Standby switch
65b . . . Imaging actuation switch
600 . . . Imaging area setting screen
611 . . . Dental arch image
700 . . . High sensitivity site specification screen
720 . . . Property display section
Bx . . . X-ray cone beam
CA . . . CT imaging area
GD . . . Area
H . . . High sensitivity site
Ha . . . Parotid gland
Hal . . . Left parotid gland
Har . . . Right parotid gland
Hb . . . Submandibular gland
Hbl . . . Left submandibular gland
Hbr . . . Right Submandibular gland
Hc . . . Thyroid gland
Im . . . Lens
L . . . Revolution range
Ls . . . Revolution start position
Le . . . Revolution end position
M1 . . . Subject

What is claimed is:

1. An X-ray CT imaging device, comprising:
a revolution section that causes an X-ray generation source and an electric X-ray detector, facing each other while having a subject therebetween, to revolve about a revolution shaft as a center of revolution;
a revolution driving section that drives driving the revolution section to revolve with respect to the subject;
an X-ray radiation area setting section that accepts a setting of a local area of the subject as an X-ray radiation area;
a control section that controls at least the revolution driving section; and
a high sensitivity site specification section to specify a high sensitivity site in a biological body that is highly sensitive to an X-ray;
wherein the revolution section is revolved with respect to the X-ray radiation area to perform CT imaging; and
wherein, when radiation of an X-ray flux in a revolving movement is performed during the CT imaging in accordance with the X-ray radiation area accepted by the X-ray radiation area setting section, the control section controls at least one of an X-ray revolution plane formed by the X-ray flux along with the revolution of the revolution section, and a revolution range of the revolution section, such that an amount of X-ray radiation toward the high sensitivity site is decreased.

2. An X-ray CT imaging device according to claim 1, wherein the high sensitivity site specification section specifies the high sensitivity site in a schematic view of a head of the subject.

3. An X-ray CT imaging device according to claim 1, wherein the control section performs revolution range control of changing at least one of an X-ray radiation start position and an X-ray radiation end position in the revolution range in accordance with the X-ray radiation area set by the X-ray radiation area setting section and the high sensitivity site.

4. An X-ray CT imaging device according to claim 1, wherein the control section performs control of changing at least one of an X-ray radiation angle with respect to a predetermined reference plane and a radiation position on the subject to control the x-ray revolution plane in accordance with the X-ray radiation area set by the X-ray radiation area setting section and the high sensitivity site.

5. An X-ray CT imaging device according to claim 4, further comprising:
a support section that supports the revolution section via the revolution shaft; and
a support section moving section that moves the support section;
wherein the support section moving section includes at least one of a shaft moving mechanism that moves the revolution shaft with respect to the support section and a relative moving mechanism that moves the support section with respect to the subject; and
wherein the control section controls the movement of the support section moving section thus to control the X-ray revolution plane.

6. An X-ray CT imaging device according to claim 4, further comprising an X-ray radiation range restriction section that restricts an X-ray radiation range, the X-ray radiation range restriction section being provided forward to the X-ray generation source in an X-ray radiation direction;
wherein the control section controls the restriction of the X-ray radiation range restriction section thus to control the X-ray revolution plane.

7. An X-ray CT imaging device according to claim 1, further comprising a control pattern storage section that stores a control pattern by the control section for each of set areas that are each set as the X-ray radiation area by the X-ray radiation area setting section.

8. An X-ray CT imaging device according to claim 1, further comprising a high sensitivity site information storage section that stores information on the high sensitivity site.

9. An X-ray CT imaging device according to claim 1, wherein the X-ray radiation area setting section displays an image containing the X-ray radiation area and accepts a setting that sets the X-ray radiation area with respect to the displayed image, and also displays the high sensitivity site as overlapping the image.

10. An X-ray CT imaging device according to claim 9, further comprising a high sensitivity site replacing section that replaces the high sensitivity site displayed as overlapping the image with another high sensitivity site.

11. An X-ray CT imaging device according to claim 1, further comprising:
an X-ray imaging preparation switch that revolves the revolution section to the X-ray radiation start position in the revolution range in accordance with the set area that is set by the X-ray radiation area setting section, the revolution range being different for each of the set areas; and
an X-ray radiation switch that directs the X-ray toward the set area while revolving the revolution section to perform imaging.

12. An X-ray CT imaging device according to claim 1, further comprising a movement driving section that moves the revolution section;
wherein the control section performs driving control that moves the revolution section with respect to the movement driving section; and
wherein, in the driving control, controls for both of the revolution of the revolution section and the movement of the revolution section caused by moving the revolution shaft by the movement driving section are performed concurrently to allow panorama X-ray imaging to be performed.

13. An X-ray CT imaging device according to claim 1, further comprising a cephalo-imaging head fixation device provided perpendicularly to a direction of the revolution shaft, and thus cephalo-X-ray imaging is allowed to be performed.

14. An X-ray CT imaging method performed by use of an X-ray CT imaging device, the X-ray CT imaging device including:
a revolution section that causes an X-ray generation source and an electric X-ray detector, facing each other while having a subject therebetween, to revolve about a revolution shaft as a center of revolution;
a revolution driving section that drives the revolution section to revolve with respect to the subject;
an X-ray radiation area setting section that accepts a setting of a local area of the subject as an X-ray radiation area; and
a control section that controls at least the revolution driving section;
wherein the revolution section is revolved with respect to the X-ray radiation area to perform CT imaging; and
wherein the X-ray CT imaging method comprising the step of, when a high sensitivity site of a biological body that is highly sensitive to an X-ray is located in an area where an X-ray flux in a revolving movement passes during the CT imaging in accordance with the X-ray radiation area accepted by the X-ray radiation area setting section, controlling at least one of an X-ray revolution plane formed by the X-ray flux along with the revolution of the revolution section and a revolution range of the revolution section, such that an amount of X-ray radiation toward the high sensitivity site is decreased in accordance with the X-ray radiation area accepted by the X-ray radiation area setting section, the control being performed by the control section.

* * * * *